(12) United States Patent
Masuda et al.

(10) Patent No.: US 8,636,532 B2
(45) Date of Patent: Jan. 28, 2014

(54) GAS SENSOR AND METHOD FOR MAKING THE SAME

(75) Inventors: Koichi Masuda, Nagoya (JP); Hirohito Kiyota, Kiyosu (JP); Nobukazu Ikoma, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 350 days.

(21) Appl. No.: 13/207,955

(22) Filed: Aug. 11, 2011

(65) Prior Publication Data

US 2012/0031171 A1 Feb. 9, 2012

Related U.S. Application Data

(63) Continuation of application No. PCT/JP2011/050843, filed on Jan. 19, 2011.

(60) Provisional application No. 61/296,079, filed on Jan. 19, 2010.

(51) Int. Cl.
*H01R 13/15* (2006.01)
*G01N 27/403* (2006.01)

(52) U.S. Cl.
USPC ...... 439/263; 204/426; 439/593; 439/620.01; 439/913

(58) Field of Classification Search
USPC ............ 439/263, 345, 346, 593, 620.21, 676, 439/913; 204/424, 426
See application file for complete search history.

(56) References Cited

U.S. PATENT DOCUMENTS

| 2,766,435 | A | * | 10/1956 | French | 439/263 |
| 4,118,094 | A | * | 10/1978 | Key | 439/635 |
| 4,834,677 | A | * | 5/1989 | Archang | 439/660 |
| 4,983,271 | A | | 1/1991 | Kato et al. | |
| 5,011,424 | A | * | 4/1991 | Simmons | 439/352 |
| 5,286,213 | A | * | 2/1994 | Altergott et al. | 439/139 |
| 5,411,406 | A | * | 5/1995 | Kondo | 439/263 |
| 5,556,526 | A | * | 9/1996 | Fukaya et al. | 204/425 |
| 6,019,625 | A | * | 2/2000 | Nimura et al. | 439/259 |

(Continued)

FOREIGN PATENT DOCUMENTS

DE 10 2006 000 500 A1 4/2007
FR 2 714 437 A1 6/1995

(Continued)

OTHER PUBLICATIONS

Extended European Search Report dated Dec. 17, 2012.

*Primary Examiner* — Lisa Caputo
*Assistant Examiner* — Punam Roy
(74) *Attorney, Agent, or Firm* — Burr & Brown, PLLC

(57) ABSTRACT

In a gas sensor, when an arithmetical mean roughness Ra of an inner periphery of a metal tube 95 is 1 μm or less and end portions 93 and 94 of U-springs 92 are formed as curved contact portions, the end portions 93 and 94 of the U-springs 92 can slide smoothly along the inner periphery of the metal tube 95. Therefore, when vibration is applied to the gas sensor, the U-springs 92 can be prevented from being caught in the inner periphery of the metal tube 95, and the vibration can be absorbed by an elastic function of the U-springs 92. Even if the gas sensor vibrates, defective contact between a sensor element 20 and contact fittings 71 and wear and cracks in the sensor element 20 are less likely to occur. That is, the gas sensor resistant to vibration can be obtained.

16 Claims, 24 Drawing Sheets

(56) References Cited

U.S. PATENT DOCUMENTS

| | | | |
|---|---|---|---|
| 6,527,573 B2 * | 3/2003 | Maga et al. | 439/260 |
| 6,672,136 B2 * | 1/2004 | Kojima | 73/31.05 |
| 7,425,138 B2 * | 9/2008 | Buhl et al. | 439/76.1 |
| 7,479,037 B2 * | 1/2009 | Bernat et al. | 439/607.41 |
| 7,563,118 B1 | 7/2009 | McCauley et al. | |
| 7,798,855 B2 * | 9/2010 | Gustin | 439/620.01 |
| 8,287,294 B2 * | 10/2012 | Masuda et al. | 439/260 |
| 2001/0025522 A1 | 10/2001 | Kojima | |
| 2004/0005820 A1 * | 1/2004 | Gutierrez et al. | 439/676 |
| 2007/0089486 A1 | 4/2007 | Yamauchi et al. | |
| 2009/0101503 A1 | 4/2009 | Kanao | |
| 2009/0156045 A1 * | 6/2009 | Gustin | 439/345 |
| 2011/0130023 A1 * | 6/2011 | Kataoka et al. | 439/271 |
| 2012/0216599 A1 * | 8/2012 | Kitoh | 73/31.05 |

FOREIGN PATENT DOCUMENTS

| | | |
|---|---|---|
| GB | 2 312 787 A | 11/1997 |
| JP | 06-037326 Y2 | 9/1994 |
| JP | 2001-343356 A1 | 12/2001 |
| JP | 2003-050225 A1 | 2/2003 |
| JP | 2007-127619 A1 | 5/2007 |
| JP | 2009-115784 A1 | 5/2009 |

* cited by examiner

FIG.14
(a)
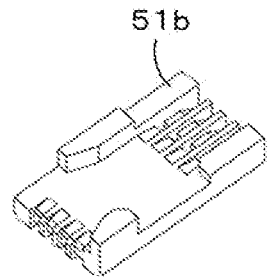
(b)
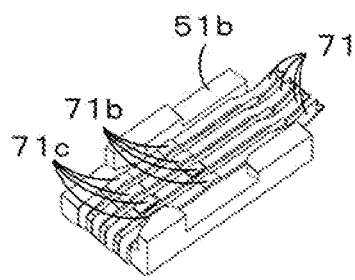
(c)
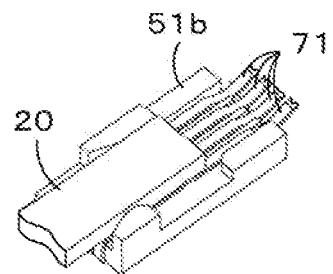

FIG.15
(a)
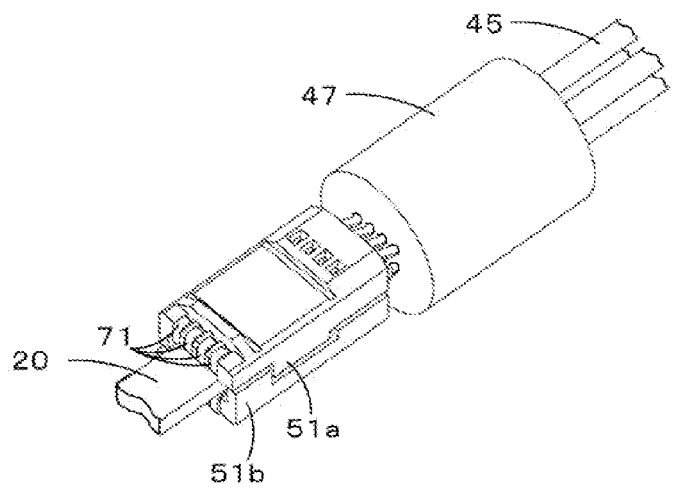
(b)
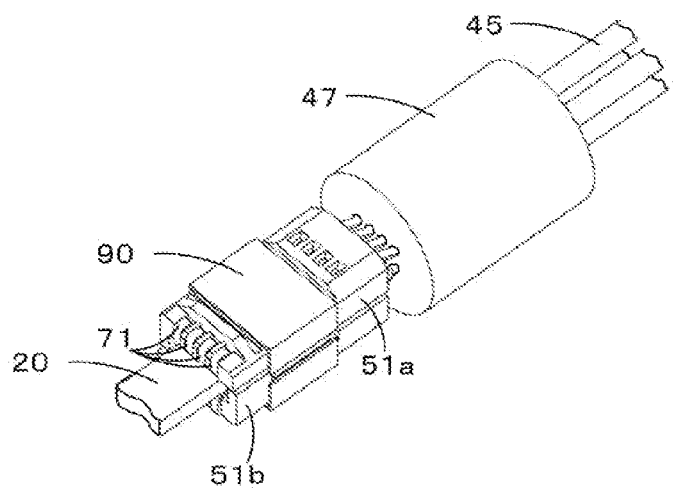
(c)
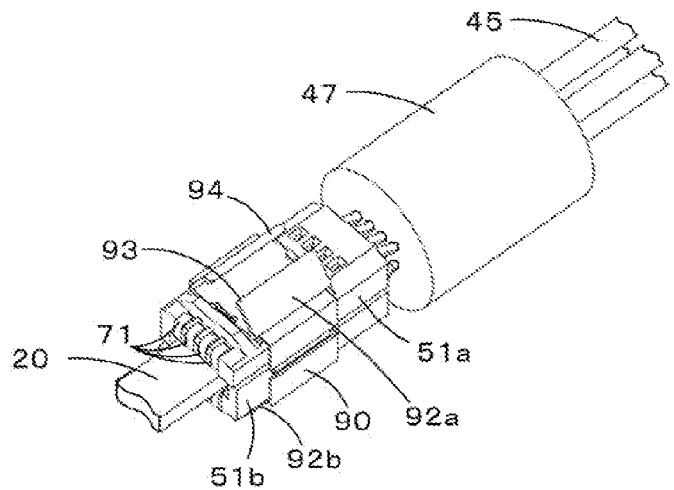

FIG.16
(a)
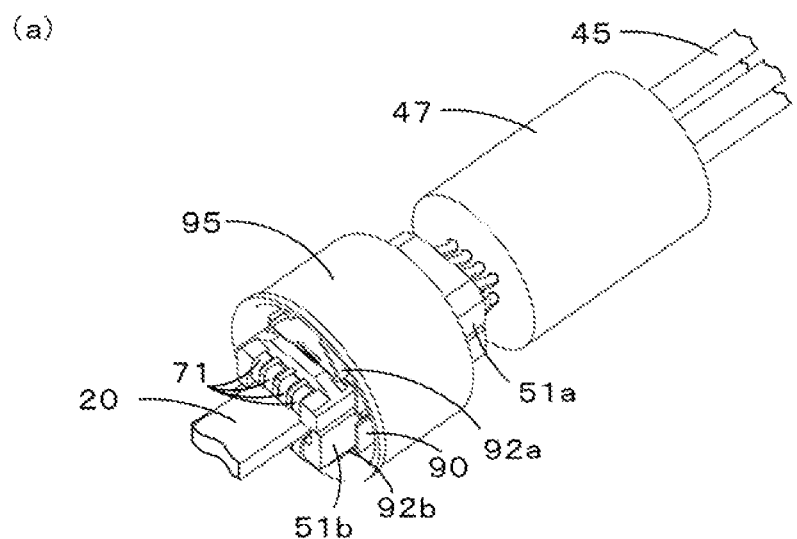
(b)
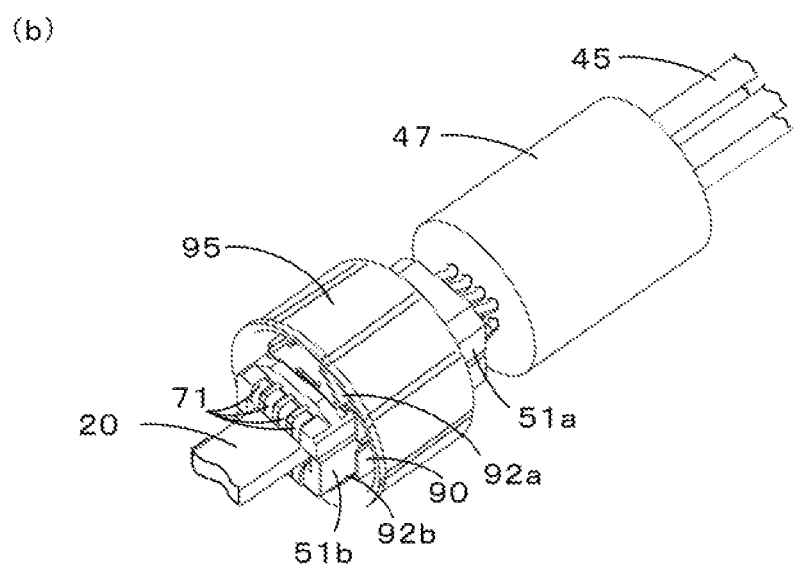

FIG.18
(a)
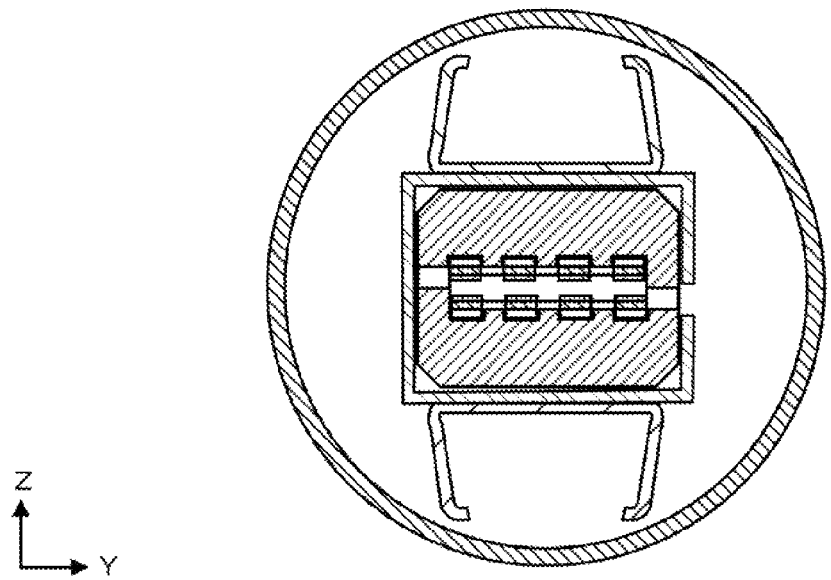
(b)
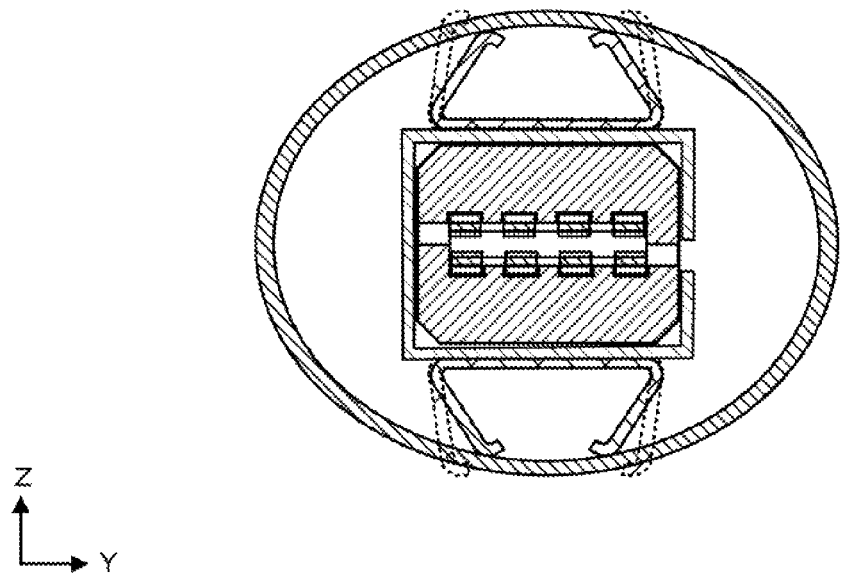

(a)

(b)

Torque                  T [Nm]
Radius of crimped ring    L [m] = 0.0052m
Coefficient of kinetic friction   $\mu$
Radial force             F [N]
Tangential force        f [N] = 250N FIG.23
(a)
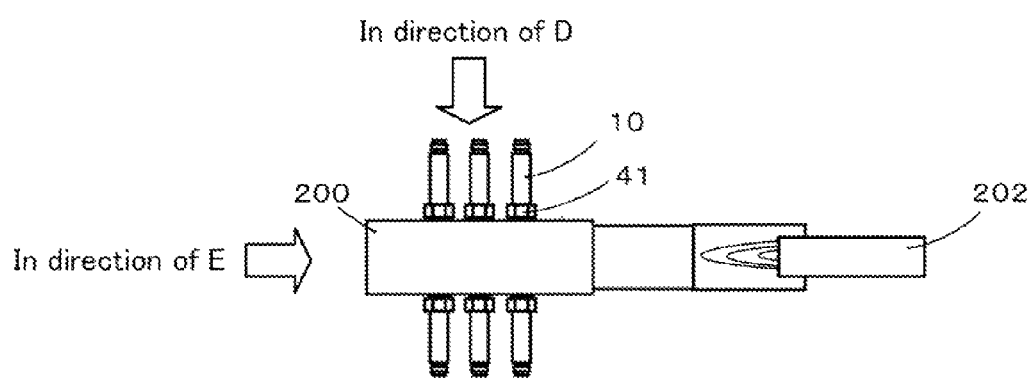
(b)
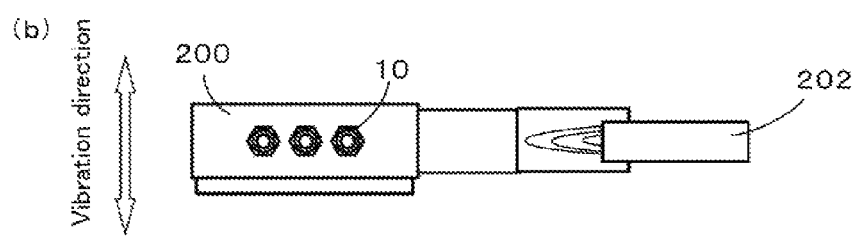
(c)
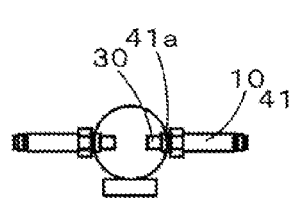

GAS SENSOR AND METHOD FOR MAKING THE SAME

TECHNICAL FIELD

The present invention relates to a gas sensor and a method for making the gas sensor.

BACKGROUND ART

Conventionally, a gas sensor has been known which detects concentrations of predetermined gas components, such as NOx and oxygen, in a gas under measurement, such as an exhaust gas from a vehicle. Such a gas sensor includes a connector for electrical connection between an external device and a sensor element that detects a gas concentration. The connector is electrically connected to a plurality of front-surface electrodes arranged side by side on a front surface of the sensor element and to a plurality of back-surface electrodes arranged side by side on a back surface of the sensor element. For example, Patent Document 1 describes a gas sensor including a planar sensor element that detects a gas concentration, lead wires, and a connector that connects the sensor element and the lead wires. FIG. 27 and FIG. 28 are an exploded perspective view and a front view, respectively, illustrating a connector 300 of such related art. As illustrated, the connector includes a plurality of long narrow contact fittings connected to lead wires 316, two housings 302a and 302b configured to hold the contact fittings, a securing fitting 304 configured to secure the housings 302a and 302b, two U-shaped pressure springs 306a and 306b attached to the securing fitting 304, and an annular metal tube 308. In the connector 300, the contact fittings 310 and a sensor element 312 are clamped between the housings 302a and 302b, which are secured by the securing fitting 304. Thus, electrodes 314 of the sensor element 312 are in contact with and are electrically connected to the contact fittings 310. Crimping the outer periphery of the metal tube 303 causes the inner periphery of the metal tube 308 to displace the pressure springs 306a and 306b. With the pressing force of the pressure springs 306a and 306b, the contact fittings 310 and the electrodes 314 are pressed under a predetermined pressure. This prevents the occurrence of defective contact between the contact fittings 310 and the electrodes 314 caused by vibration.

Patent Document 1: Japanese Examined Utility Model Registration Application Publication No. 6-37326 (FIG. 1(b))

DISCLOSURE OF INVENTION

However, depending on the condition of areas where the inner periphery of the metal tube is in contact with the pressure springs, the pressure springs may be caught and stuck inside the metal tube during vibration and may be unable to sufficiently perform an elastic function. For example, for the pressure springs to perform an elastic function when an upward force in FIG. 28 is applied to the sensor element by vibration, it is necessary that both ends of the U-shape of each pressure spring slide along the inner periphery of the metal tube and be displaced closer to each other. However, if both ends of the pressure spring are caught inside the metal tube, a sufficient elastic function cannot be performed because the displacement of both ends of the U-shape of the pressure spring is blocked. In such a case, vibration cannot be absorbed by the pressure springs. Therefore, if the sensor element and the connector including the contact fittings are secured together as a single unit and subjected to vibration for a long period of time, defective contact may occur between the contact fittings and the electrodes, or the sensor element may be worn or cracked.

The present invention has been made to solve the problem described above. A primary object of the present invention is to provide a gas sensor resistant to vibration.

To achieve the primary object described above, the present invention adopts the following means.

A first gas sensor of the present invention includes:

a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;

a plurality of long narrow first contact fittings having conducting portions in contact with the plurality of front-surface electrodes of the sensor element;

a plurality of long narrow second contact fittings having conducting portions in contact with the plurality of back-surface electrodes of the sensor element;

a first housing made of ceramic and configured to hold the plurality of first contact fittings such that the first contact fittings are arranged in a direction substantially orthogonal to the length of the first contact fittings and face the plurality of front-surface electrodes;

a second housing made of ceramic and configured to hold the plurality of second contact fittings such that the second contact fittings are arranged in a direction substantially orthogonal to the length of the second contact fittings and face the plurality of back-surface electrodes;

a cylindrical metal tube having a central axis along the length of the sensor element and disposed around the first housing and the second housing;

a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and a second elastic member substantially U-shaped in cross section, in contact with the inner periphery of the metal tube at both ends of the U-shape, and configured to press the second housing with an elastic force generated by pressure from the metal tube to bring the second housing closer to the first housing, with the sensor element interposed between the first housing and the second housing, wherein an arithmetical mean roughness Ra of the inner periphery of the metal tube is 1 μm or less;

at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube; and at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube.

In the gas sensor described above, Ra of the inner periphery of the metal tube is 1 μm or less. At the same time, at least one of both the ends of the U-shape of each of the first elastic member and the second elastic member in contact with the inner periphery of the metal tube is a curved contact portion.

This improves sliding of the first elastic member and the second elastic member along the inner periphery of the metal tube. Thus, when vibration is applied to the gas sensor, the first elastic member and the second elastic member can be prevented from being caught in the inner periphery of the metal tube, and the vibration can be absorbed by an elastic function of the first elastic member and the second elastic member. Even when the gas sensor vibrates, defective contact between the sensor element and the first and second contact fittings and wear and cracks in the sensor element are less likely to occur. That is, the gas sensor resistant to vibration can be obtained. In this case, the sensor element may be a planar element.

In the first gas sensor of the present invention, the arithmetical mean roughness Ra of the inner periphery of the metal tube may be 0.8 μm or less. If the arithmetical mean roughness Ra of the inner periphery of the metal tube is 0.8 μm or less, the sliding of the first elastic member and the second elastic member along the inner periphery of the metal tube is further improved, and hence the gas sensor more resistant to vibration can be obtained. There is no lower limit to the range of arithmetical mean roughness Ra of the inner periphery of the metal tube. The smaller the value of Ra, the better the sliding of the first elastic member and the second elastic member along the inner periphery of the metal tube.

In the first gas sensor of the present invention, the inner periphery of the metal tube may be plated, coated with fluororesin, coated with liquid lubricant, or coated with solid lubricant. This further improves the sliding of the first elastic member and the second elastic member along the inner periphery of the metal tube, and hence the gas sensor more resistant to vibration can be obtained.

In the first gas sensor of the present invention, in the first elastic member and the second elastic member, the curved surface of the curved contact portion in contact with the inner periphery of the metal tube may be plated, coated with fluororesin, coated with liquid lubricant, or coated with solid lubricant. This further improves the sliding of the first elastic member and the second elastic member along the inner periphery of the metal tube, and hence the gas sensor more resistant to vibration can be obtained.

In the first gas sensor of the present invention, the metal tube may be a member formed by crimping an outer periphery thereof to reduce an inside diameter thereof.

In the first gas sensor of the present invention, both the ends of the first elastic member may be formed as curved contact portions, and both the ends of the second elastic member may be formed as curved contact portions. Thus, as compared to the case where only one of both the ends of the U-shape of each of the first elastic member and the second elastic member is formed as a curved contact portion, the sliding of the first elastic member and the second elastic member along the inner periphery of the metal tube is better.

In the first gas sensor of the present invention, the conducting portions of the first contact fittings and the second contact fittings may be elastic bodies. At the same time, the sensor element may be clamped with a pressing force generated by elastic deformation of the conducting portions of the first contact fittings caused by a pressing force applied from the first elastic member through the first housing, and with a pressing force generated by elastic deformation of the conducting portions of the second contact fittings caused by a pressing force applied from the second elastic member through the second housing. Thus, since the conducting portions clamp the sensor element with the pressing forces generated by elastic deformation, it is less likely that poor contact will occur between the sensor element and the first and second contact fittings.

The first gas sensor of the present invention may further include a third elastic member configured to clamp and press the first housing and the second housing closer to each other. This makes it less likely that poor contact will occur between the sensor element and the first and second contact fittings.

A second gas sensor of the present invention includes:

a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;

a plurality of long narrow first contact fittings having conducting portions in contact with the plurality of front-surface electrodes of the sensor element;

a plurality of long narrow second contact fittings having conducting portions in contact with the plurality of back-surface electrodes of the sensor element;

a first housing made of ceramic and configured to hold the plurality of first contact fittings such that the first contact fittings are arranged in a direction substantially orthogonal to the length of the first contact fittings and face the plurality of front-surface electrodes;

a second housing made of ceramic and configured to hold the plurality of second contact fittings such that the second contact fittings are arranged in a direction substantially orthogonal to the length of the second contact fittings and face the plurality of back-surface electrodes;

a cylindrical metal tube having a central axis along the length of the sensor element and disposed around the first housing and the second housing;

a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and a second elastic member substantially U-shaped in cross section, in contact with the inner periphery of the metal tube at both ends of the U-shape, and configured to press the second housing with an elastic force generated by pressure from the metal tube to bring the second housing closer to the first housing, with the sensor element interposed between the first housing and the second housing, wherein the inner periphery of the metal tube is plated, coated with fluororesin, coated with liquid lubricant, or coated with solid lubricant;

at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube; and at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube.

In the gas sensor described above, the inner periphery of the metal tube may be plated, coated with fluororesin, coated with liquid lubricant, or coated with solid lubricant. At the same time, at least one of both the ends of the U-shape of each of the first elastic member and the second elastic member in contact with the inner periphery of the metal tube is a curved contact portion. This improves sliding of the first elastic member and the second elastic member along the inner periphery of the metal tube. Thus, as in the case of the first gas sensor of the present invention described above, the gas sensor resistant to vibration can be obtained.

A third gas sensor of the present invention includes:

a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;

a plurality of long narrow first contact fittings having conducting portions in contact with the plurality of front-surface electrodes of the sensor element;

a plurality of long narrow second contact fittings having conducting portions in contact with the plurality of back-surface electrodes of the sensor element;

a first housing made of ceramic and configured to hold the plurality of first contact fittings such that the first contact fittings are arranged in a direction substantially orthogonal to the length of the first contact fittings and face the plurality of front-surface electrodes;

a second housing made of ceramic and configured to hold the plurality of second contact fittings such that the second contact fittings are arranged in a direction substantially orthogonal to the length of the second contact fittings and face the plurality of back-surface electrodes;

a cylindrical metal tube having a central axis along the length of the sensor element and disposed around the first housing and the second housing;

a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and a second elastic member substantially U-shaped in cross section, in contact with the inner periphery of the metal tube at both ends of the U-shape, and configured to press the second housing with an elastic force generated by pressure from the metal tube to bring the second housing closer to the first housing, with the sensor element interposed between the first housing and the second housing, wherein at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube;

at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube; and in the first elastic member and the second elastic member, the curved surface of the curved contact portion in contact with the inner periphery of the metal tube is plated, coated with fluororesin, coated with liquid lubricant, or coated with solid lubricant.

In the gas sensor described above, in the first elastic member and the second elastic member, the curved surface of the curved contact portion in contact with the inner periphery of the metal tube is plated, coated with fluororesin, coated with liquid lubricant, or coated with solid lubricant. At the same time, at least one of both the ends of the U-shape of each of the first elastic member and the second elastic member in contact with the inner periphery of the metal tube is a curved contact portion. This improves sliding of the first elastic member and the second elastic member along the inner periphery of the metal tube. Thus, as in the case of the first gas sensor of the present invention described above, the gas sensor resistant to vibration can be obtained.

A method for making a gas sensor of the present invention includes the steps of:

(a) preparing a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof; a plurality of long narrow first contact fittings having conducting portions in contact with the plurality of front-surface electrodes of the sensor element; a plurality of long narrow second contact fittings having conducting portions in contact with the plurality of back-surface electrodes of the sensor element; a first housing made of ceramic and configured to hold the plurality of first contact fittings such that the first contact fittings are arranged in a direction substantially orthogonal to the length of the first contact fittings and face the plurality of front-surface electrodes; and a second housing made of ceramic and configured to hold the plurality of second contact fittings such that the second contact fittings are arranged in a direction substantially orthogonal to the length of the second contact fittings and face the plurality of back-surface electrodes;

(b) positioning a cylindrical metal tube having an inner periphery with an arithmetical mean roughness Ra of 1 μm or less, a first elastic member substantially U-shaped in cross section and formed such that at least one of both ends of the U-shape is a curved contact portion having a curved surface, and a second elastic member substantially U-shaped in cross section and formed such that at least one of both ends of the U-shape is a curved contact portion having a curved surface, such that the metal tube is disposed around the first housing and the second housing and a central axis of the metal tube is along the length of the sensor element, the first elastic member is disposed between the metal tube and the first housing, and the second elastic member is disposed between the metal tube and the second housing; and (c) plastically deforming the metal tube by inwardly pressing the metal tube such that the first elastic member presses the first housing with an elastic force generated when both the ends of the first elastic member are pressed by the metal tube, and brings the first housing closer to the second housing, with the sensor element interposed between the first housing and the second housing; and that the second elastic member presses the second housing with an elastic force generated when both the ends of the second elastic member are pressed by the metal tube, and brings the second housing closer to the first housing, with the sensor element interposed between the first housing and the second housing, wherein the curved surface of each of the curved contact portion of the first elastic member and the curved contact portion of the second elastic member is in contact with the inner periphery of the metal tube plastically deformed in the step (c), and a curvature radius of the curved surface is smaller than or equal to a curvature radius of the contact portion of the inner periphery of the metal tube.

In the above-described method for making a gas sensor, Ra of the inner periphery of the metal tube is 1 μm or less. At the same time, at least one of both the ends of the U-shape of each of the first elastic member and the second elastic member in contact with the inner periphery of the metal tube is a curved contact portion. Thus, as in the case of the first gas sensor of the present invention described above, the sliding of the first elastic member and the second elastic member along the inner periphery of the metal tube is improved, and hence vibration can be absorbed by an elastic function of the first elastic member and the second elastic member. The gas sensor resistant to vibration can thus be obtained. As described above, the first elastic member and the second elastic member can slide smoothly along the inner periphery of the metal tube. Therefore, when the metal tube is plastically deformed by inwardly pressing the outer periphery of the metal tube in the step (c), the first elastic member and the second elastic member can be prevented from being caught in the inner periphery of the metal tube and unevenly deformed. Thus, since it is possible to prevent uneven contact between the sensor element and the first and second contact fittings caused by a biased elastic force of the first and second elastic members, it is less likely that poor contact will occur between the sensor element and the first and second contact fittings during vibration. The gas sensor resistant to vibration can thus be obtained.

BRIEF DESCRIPTION OF DRAWINGS

FIG. 8 illustrates a positional relationship between contact fittings 71 and a sensor element 20 as viewed from a first housing 51a.

FIG. 14 is a perspective view schematically illustrating a process of making the connector 50.

FIG. 15 is another perspective view schematically illustrating the process of making the connector 50.

FIG. 16 is another perspective view schematically illustrating the process of making the connector 50.

FIG. 18 illustrates how the metal tube 95 is plastically deformed.

FIG. 23 illustrates a heat vibration test.

BEST MODES FOR CARRYING OUT THE INVENTION

Embodiments of the present invention will now be described with reference to the drawings.

Figure 1:
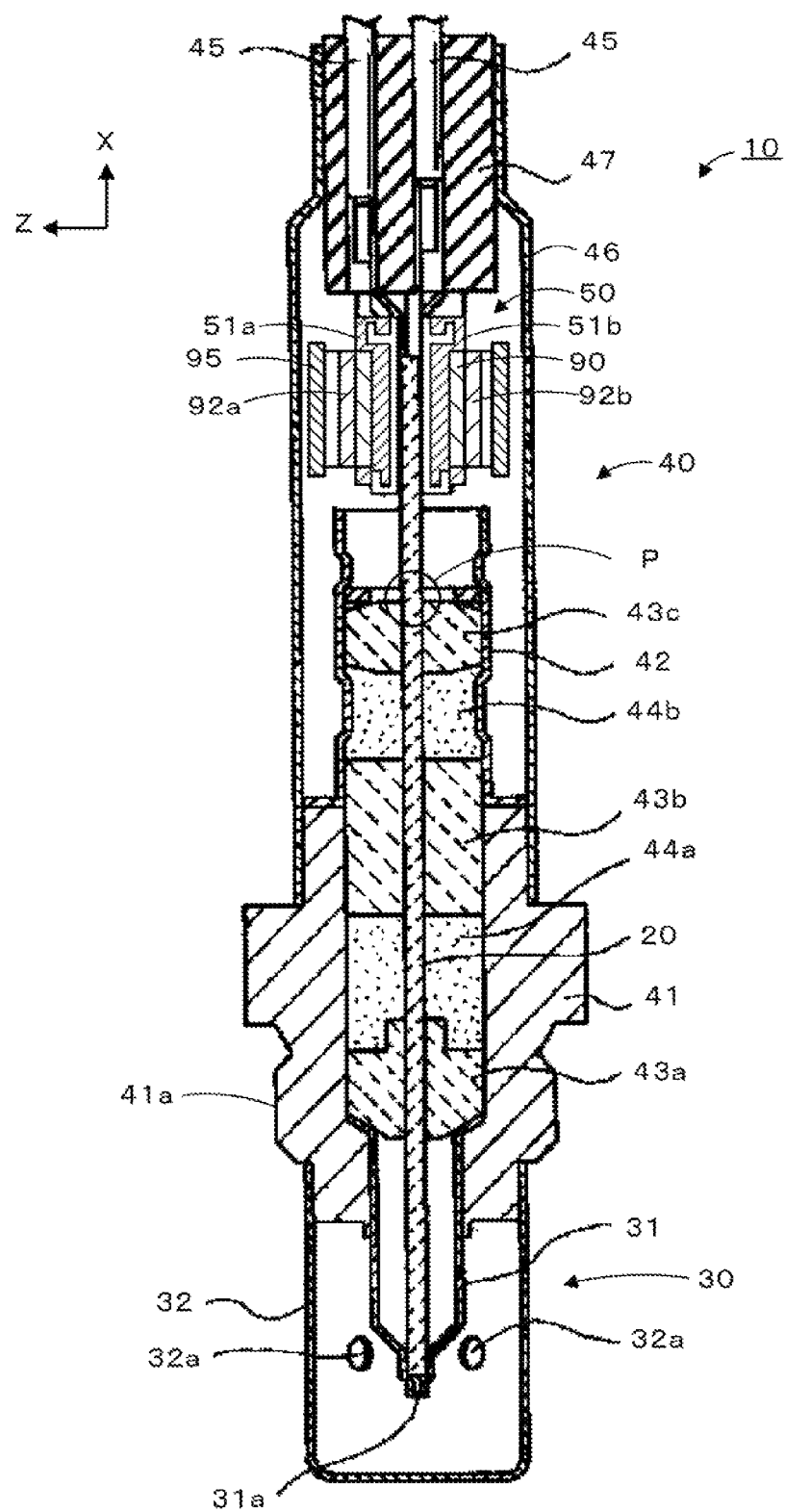
FIG. 1 is a longitudinal cross-sectional view of a gas sensor 10 according to the present embodiment.
Figure 2:
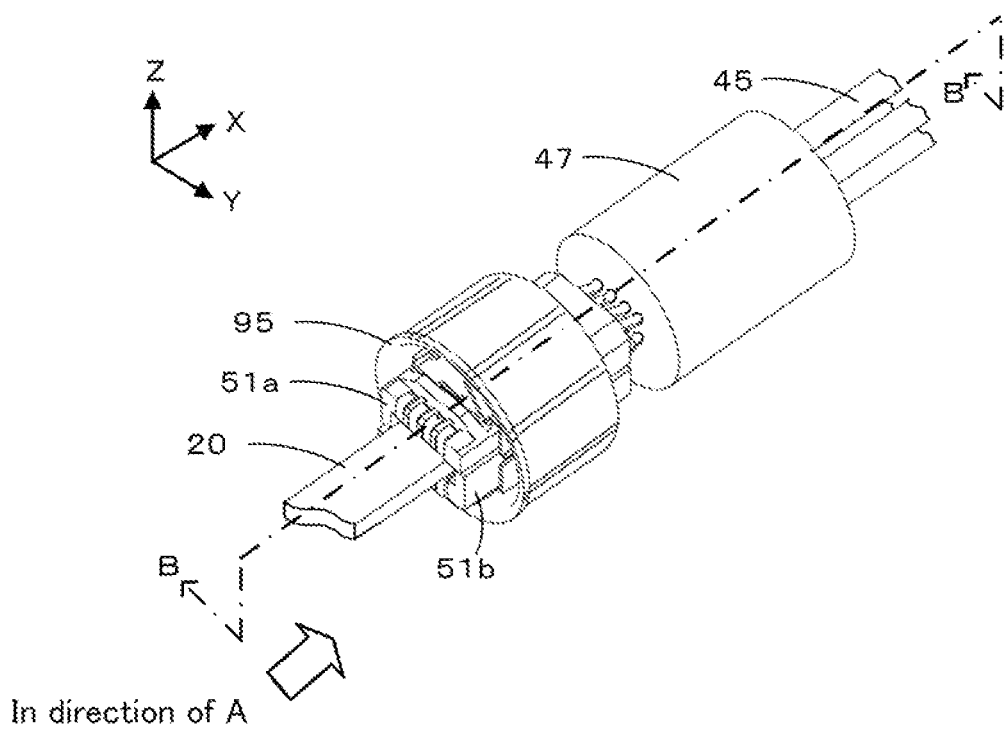
FIG. 2 is a perspective view of a connector 50.
Figure 3:
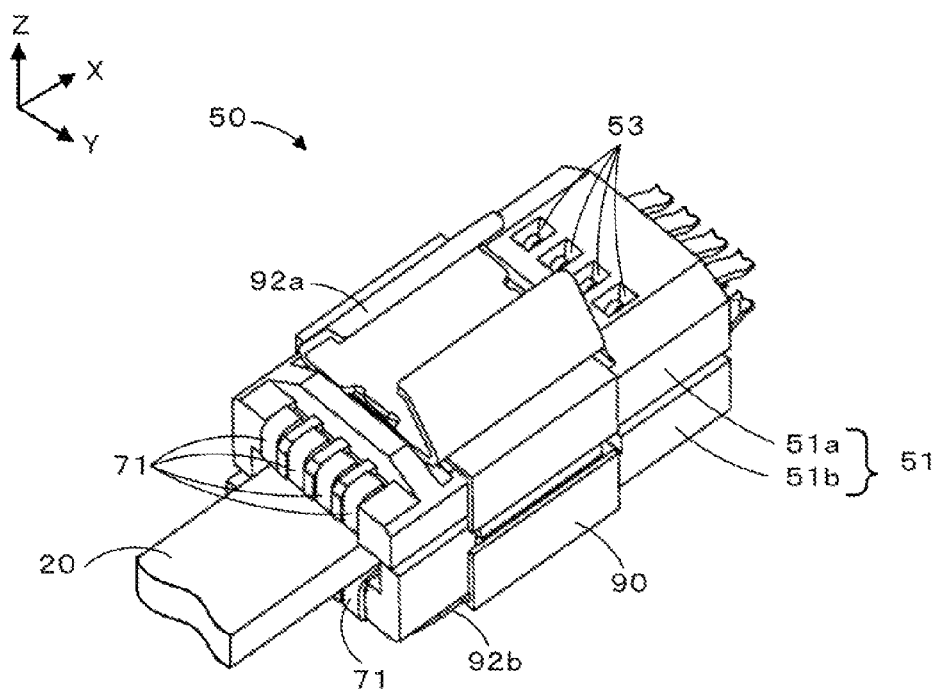
FIG. 3 is a perspective view illustrating the connector 50 of FIG. 2 without a metal tube 95.
Figure 4:
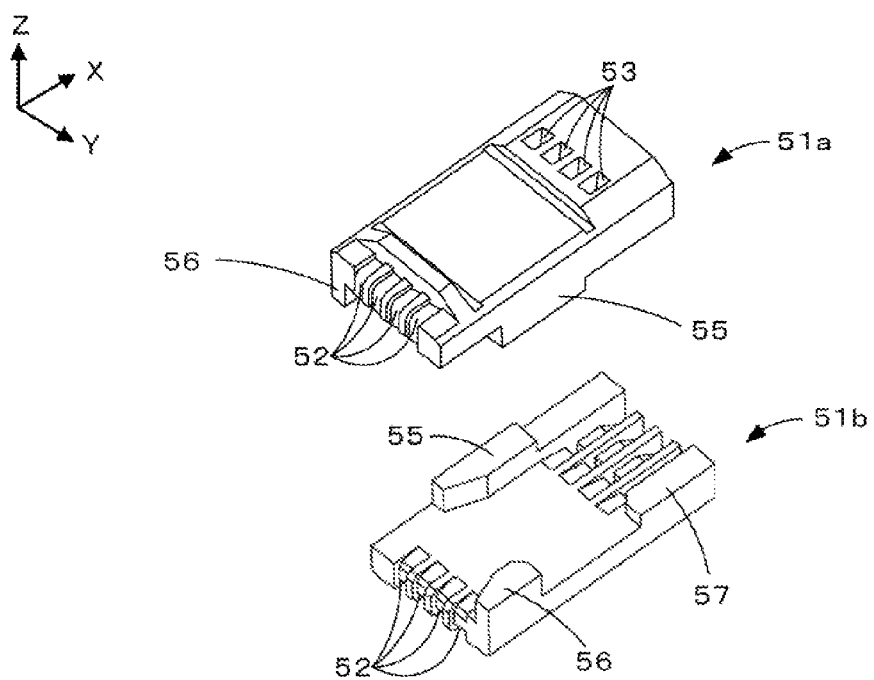
FIG. 4 is an exploded perspective view illustrating housings 51 of the connector 50.
Figure 5:
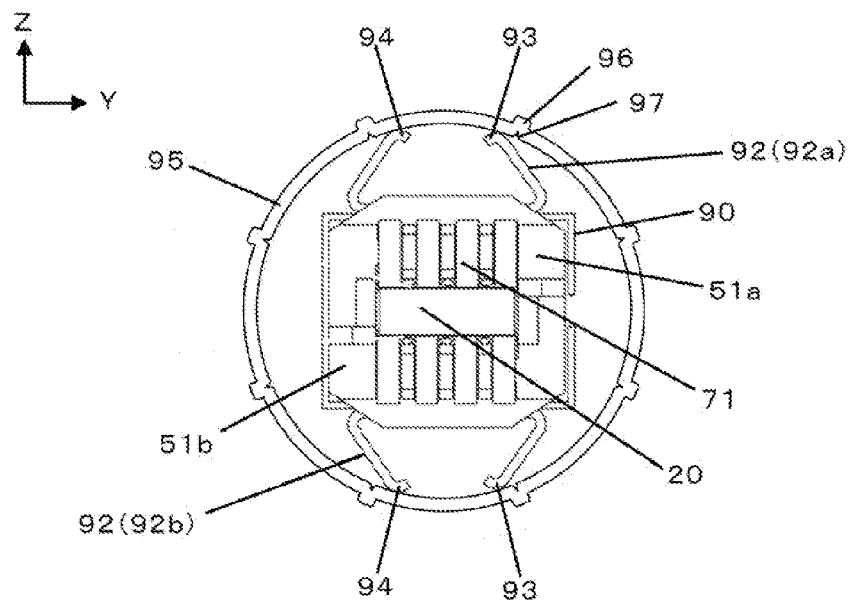
FIG. 5 is a diagram as viewed in the direction of A in FIG. 2.
Figure 6:
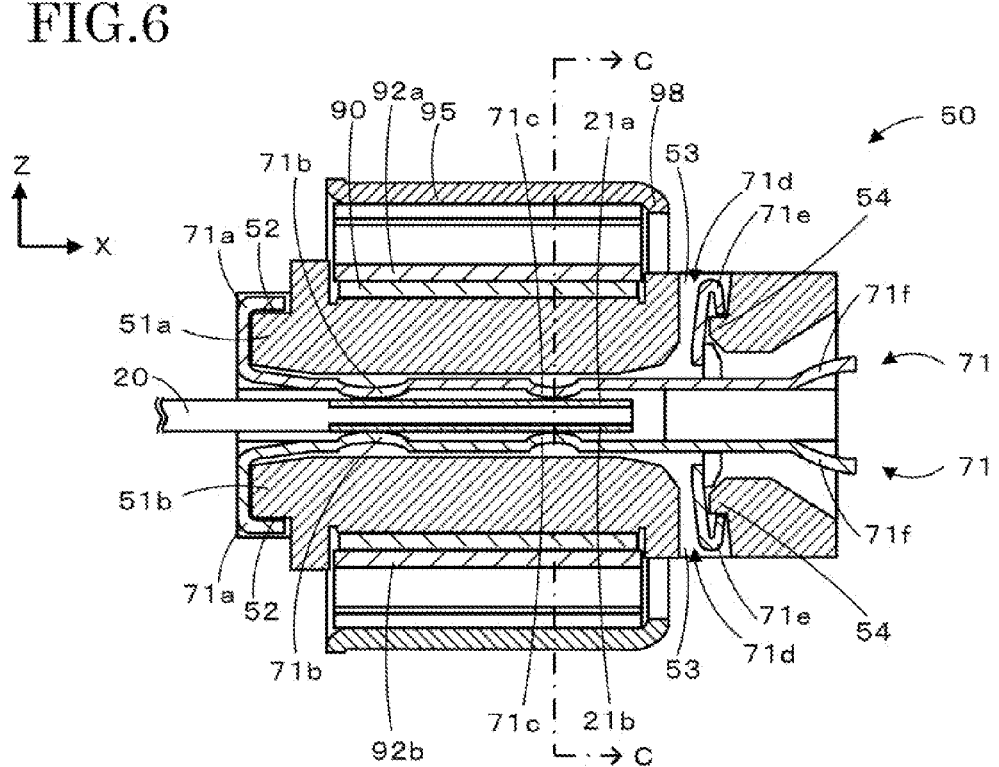
FIG. 6 is a cross-sectional view taken along line B-B in FIG. 2.
Figure 7:
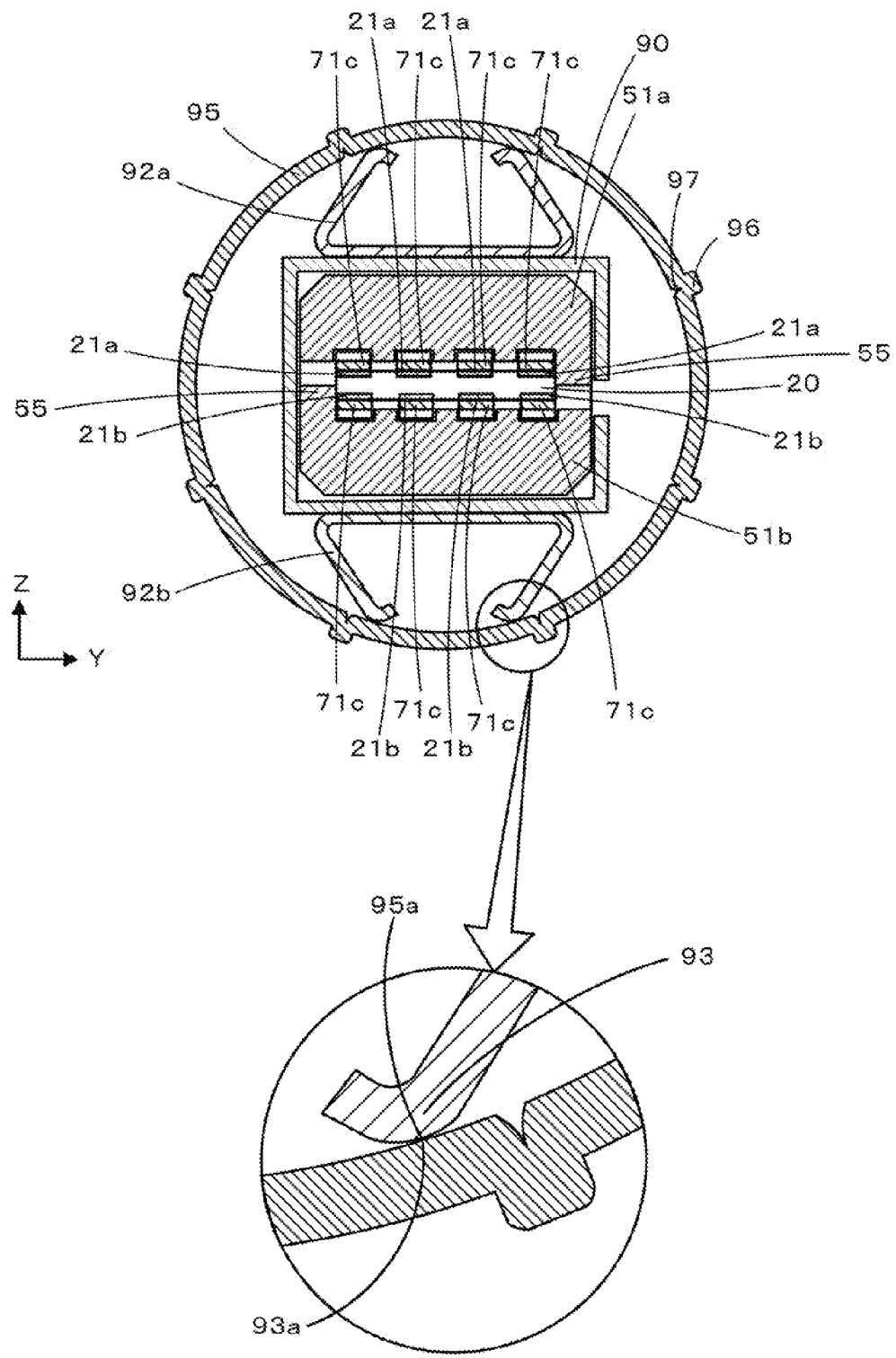
FIG. 7 is a cross-sectional view taken along line C-C in FIG. 6.
Figure 8:
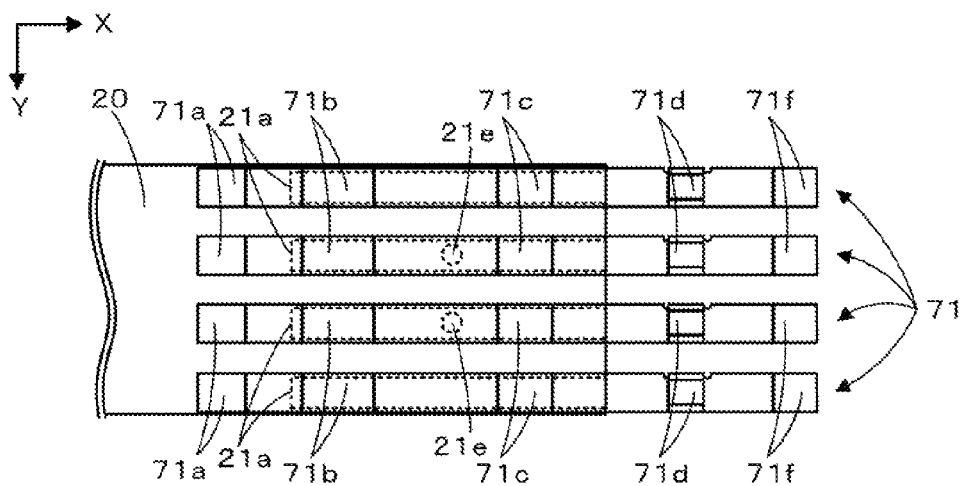
Figure 9:
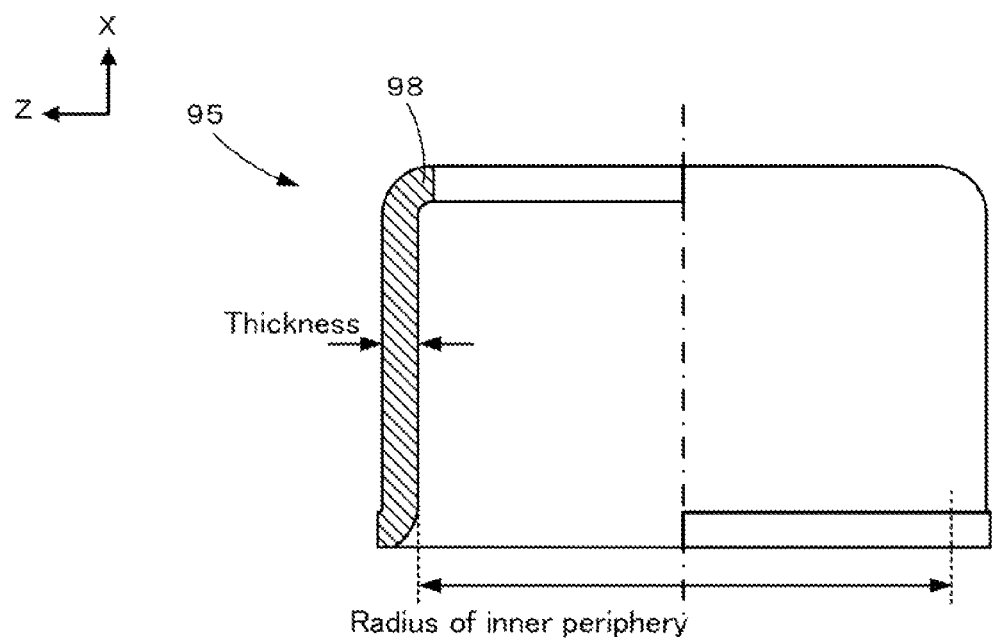
FIG. 9 is a broken-out cross-sectional view of the metal tube 95.
Figure 10:
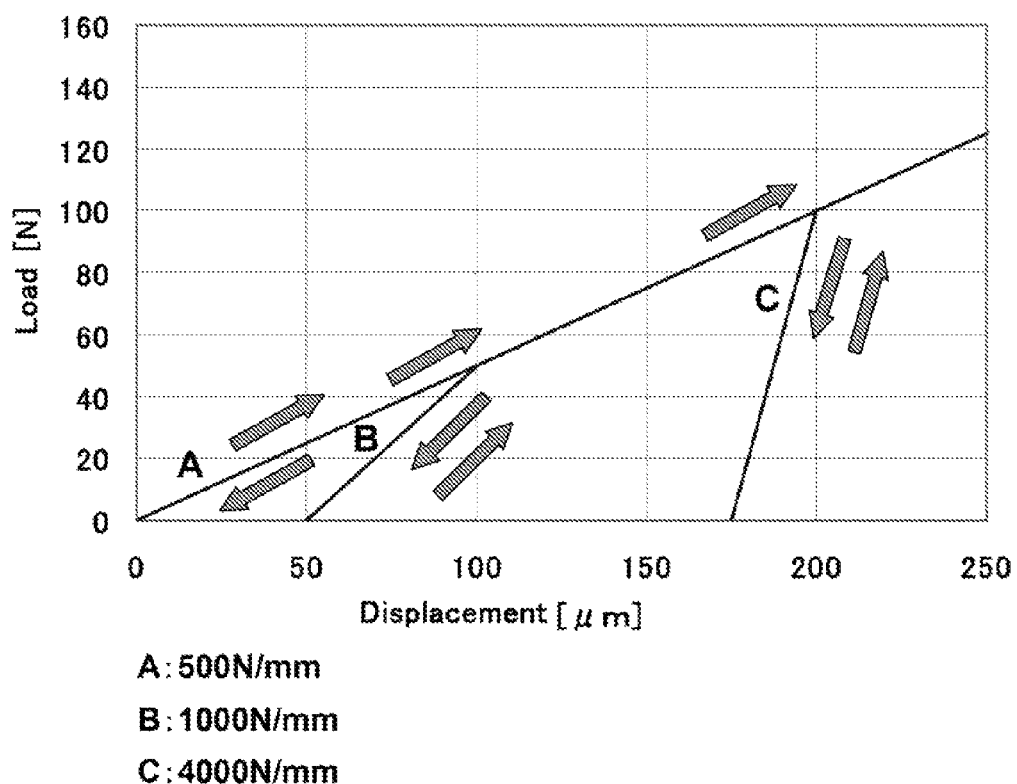
FIG. 10 is a graph showing a relationship between load and displacement of a supporting portion 71b and a conducting portion 71c.
Figure 11:
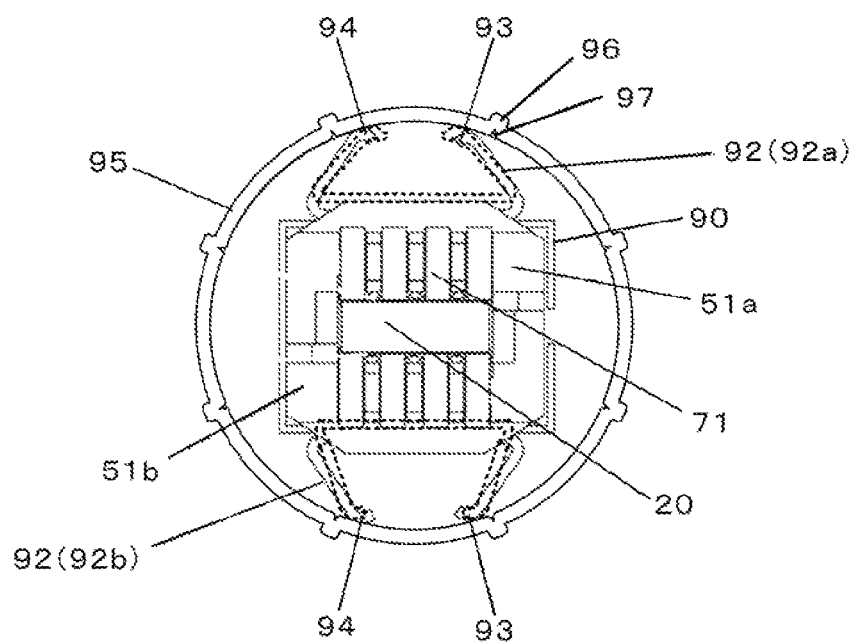
FIG. 11 illustrates the conditions of the sensor element 20 and the connector 50 during vibration.
Figure 12:
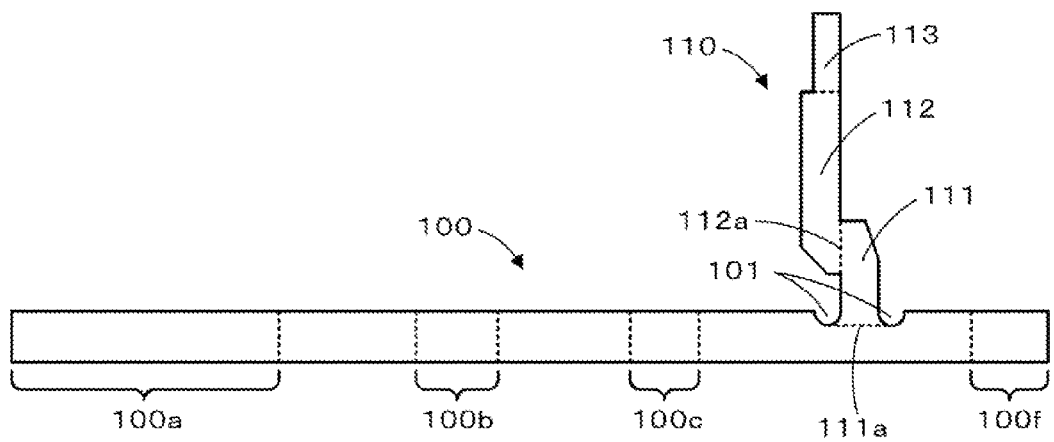
FIG. 12 illustrates a contact fitting 71 before being bent.
Figure 13:
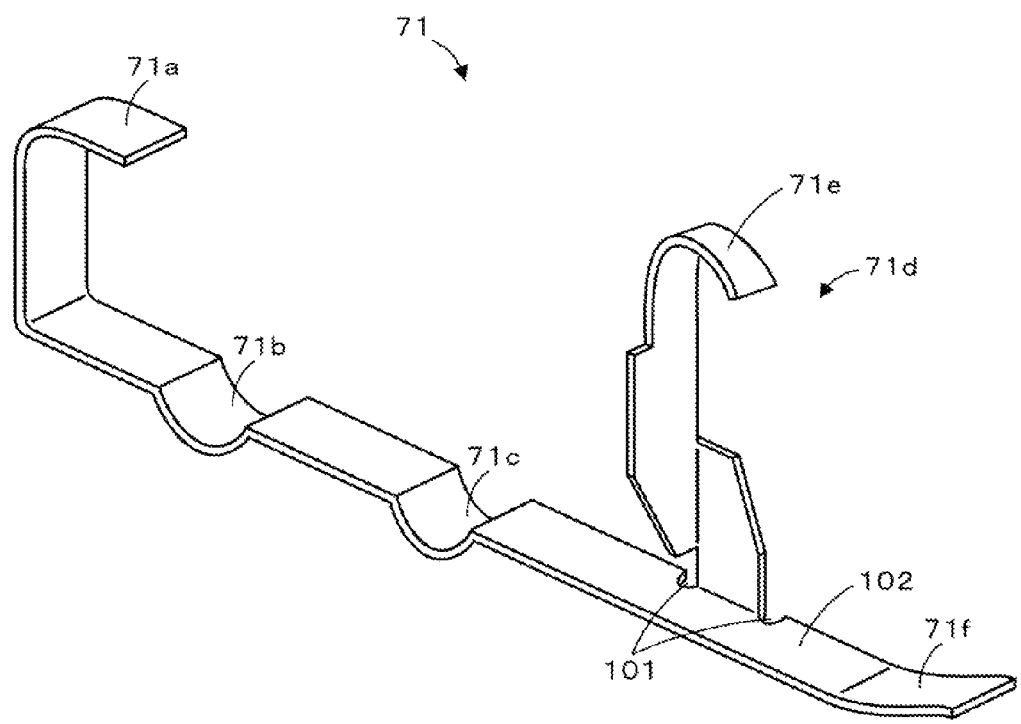
FIG. 13 illustrates a bent contact fitting 71.

FIG. 1 is a longitudinal cross-sectional view of a gas sensor 10 according to an embodiment of the present invention. FIG. 2 is a perspective view of a connector 50. FIG. 3 is a perspective view illustrating the connector 50 of FIG. 2 without a metal tube 95. FIG. 4 is an exploded perspective view illustrating housings 51 of the connector 50. FIG. 5 is a diagram as viewed in the direction of A in FIG. 2. FIG. 6 is a cross-sectional view taken along line B-B in FIG. 2. FIG. 7 is a cross-sectional view taken along line C-C in FIG. 6. FIG. 8 illustrates a positional relationship between contact fittings 71 and a sensor element 20 as viewed from a first housing 51a. FIG. 9 is a broken-out cross-sectional view of the metal tube 95. FIG. 10 is a graph showing a relationship between load and displacement of a supporting portion 71b and a conducting portion 71c. FIG. 11 illustrates the sensor element 20 and the connector 50 during vibration. FIG. 12 illustrates a contact fitting 71 before being bent. FIG. 13 illustrates a bent contact fitting 71.

As illustrated in FIG. 1, the gas sensor 10 includes the sensor element 20 that measures a predetermined gas component in gas under measurement, a protective cover 30 that protects an end portion of the sensor element 20, and a sensor assembly 40 that includes the connector 50 electrically connected to the sensor element 20. For example, the gas sensor 10 is attached to an exhaust gas pipe of a vehicle and used to measure gas components, such as NOx and $O_2$, contained in exhaust gas, which is gas under measurement.

The sensor element 2C is a long narrow planar element. The sensor element 20 is formed by stacking, for example, six ceramic substrates composed of oxygen-ion conductive solid electrolyte layers, such as zirconia ($ZrO_2$) layers. An end portion of the sensor element 20 adjacent to the protective cover 30 is referred to as a tip end, and the other end portion of the sensor element 20 adjacent to the connector 50 is referred to as a base end. As illustrated in FIG. 7, four front-surface electrodes 21a and four back-surface electrodes 21b are formed on front and back surfaces of the base end of the sensor element 20. The front-surface electrodes 21a and the back-surface electrodes 21b are collectively referred to as electrodes 21. The electrodes 21 are for applying a voltage to the sensor element 20, and for deriving electromotive force or current which is generated in accordance with the concentration of a gas component detected by the sensor element 20. The electrodes 21 are electrically connected, through electric paths inside the sensor element 20, to electrodes (not shown) within the tip end of the sensor element 20. The positions of the front-surface electrodes 21a and the back-surface electrodes 21b will be described later on.

As illustrated in FIG. 1, the protective cover 30 is disposed around the tip end of the sensor element 20. The protective cover 30 includes an inner protective cover 31 that covers the tip end of the sensor element 20, and an outer protective cover 32 that covers the inner protective cover 31. The inner protective cover 31 has a cylindrical shape and is provided with an inner protective cover hole 31a, at the tip end of the sensor element 20, for introducing gas under measurement. The outer protective cover 32 has a cylindrical shape with a bottom and is provided with outer protective cover holes 32a, in the periphery thereof, for introducing gas under measurement. The inner protective cover 31 and the outer protective cover 32 are made of metal, such as stainless steel.

The sensor assembly 40 includes a main fitting 41 made of metal, an inner cylinder 42 and an outer cylinder 46 having a cylindrical shape and secured by welding to the main fitting 41, and the connector 50 connected to the base end of the sensor element 20. The main fitting 41 can be attached, for example, to an exhaust gas pipe of a vehicle with an external thread 41a. The inner cylinder 42 contains a plurality of ceramic supporters 43a to 43c, and ceramic powder 44a and 44b, such as talc powder, with which a space between the ceramic supporters 43a and 43b and a space between the ceramic supporters 43b and 43c are filled. The inner cylinder 42, the sensor element 20, and the connector 50 are surrounded by the outer cylinder 46. Lead wires 45 connected to the connector 50 are pulled out of the outer cylinder 46. The lead wires 45 are electrically connected through the connector 50 to the electrodes 21 of the sensor element 20. Gaps between the outer cylinder 46 and the lead wires 45 are sealed with a rubber stopper 47. The sensor element 20 passes through the ceramic supporters 43a to 43c and the ceramic powder 44a and 44b, and is secured mainly by the main fitting 41 and the ceramic powder 44a and 44b. Therefore, for example, if the gas sensor 10 is installed in a vibrating environment such as in a vehicle, a part of the sensor element 20 on one side of an upper end portion P adjacent to the connector 50, the connector 50, and the lead wires 45 vibrate with respect to the upper end portion P of the ceramic supporter 43c. On the other hand, a part of the sensor element 20 on the other side of the upper end portion P adjacent to the protective cover 30 is less affected by vibration, as it is covered with the main fitting 41 and the ceramic powder 44a and 44b.

The connector 50 will now be described in detail. As illustrated in FIG. 5, the connector 50 includes the first housing 51a and a second housing 51b, the contact fittings 71, a securing fitting 90, a first U-spring 92a, a second U-spring 92b, and the metal tube 95.

The first housing 51a and the second housing 51b made of ceramic such as sintered alumina, each are configured to hold four contact fittings 71 arranged in a direction (Y direction) orthogonal to the length (X direction) of the contact fittings 71. The same components in the first housing 51a and the second housing 51b, which are of the same shape, are denoted by the same reference numerals. The first housing 51a and the second housing 51b are collectively referred to as the housings 51. As illustrated in FIG. 4, each housing 51 includes four retaining grooves 52 for retaining the contact fittings 71, four insertion holes 53 for insertion of the contact fittings 71, and retainers 54 formed in the respective insertion holes 53 and retaining the contact fittings 71. Each housing 51 has a protrusion 55 in one side thereof and regulating members 56 and 57 in the other side thereof in the Y direction, with the sensor element 20 interposed therebetween. The regulating members 56 and 57 regulate the relative position of first housing 51a and the second housing 51b in the X direction (see FIG. 4). The protrusion 55 is configured to fit in an indentation between the regulating member 56 and the regulating member 57 of the opposite housing 51 and thus, the relative position of the first housing 51a and the second housing 51b in the X direction can be regulated.

As illustrated in FIG. 6, the contact fittings 71 are held by the housing 51 at positions where they face the respective electrodes 21 of the sensor element 20. As illustrated in FIG. 13, each of the contact fittings 71 includes a tip portion 71a having a curved shape and retained by the retaining groove 52, a supporting portion 71b bending toward the sensor element 20 to come into contact with the electrode 21, a conducting portion 71c bending toward the sensor element 20 to come into contact with the electrode 21, an upright portion 71d in the insertion hole 53, and a connecting portion 71f pulled out of the connector 50 and electrically connected to the lead wire 45. The supporting portion 71b and the conducting portions 71c of the contact fittings 71 held by the first housing 51a are in contact with the respective front-surface electrodes 21a of the sensor element 20, while the supporting portion 71b and the conducting portions 71c of the contact fittings 71 held by the second housing 51b are in contact with the respective back-surface electrodes 21b of the sensor element 20 (see FIG. 6 and FIG. 7). Each upright portion 71d has a hook 71e having a curved shape and retained by the retainer 54.

The positional relationship between the contact fittings 71 and the electrodes 21 of the sensor element 20 will now be described. As illustrated in FIG. 6 and FIG. 8, the front-surface electrodes 21a of the sensor element 20 extend from the base end of the sensor element 20 to a position opposite the supporting portions 71b. Of the four front-surface electrodes 21a arranged in the Y direction, two front-surface electrodes 21a in the middle are electrically connected to respective through holes 21e formed for electrical connection to the electric paths inside the sensor element 20. As illustrated in FIG. 8, each of the through holes 21e is at a position between the conducting portion 71c and the supporting portion 71b. Note that the positional relationship between the back-surface electrodes 21b and the contact fittings 71, and the positions of through holes 21e electrically connected to respective back-surface electrodes 21b are the same as this, and thus will not be described here.

The first U-spring 92a is a metal elastic member substantially U-shaped in cross section and configured to press the first housing 51a through the securing fitting 90. The second U-spring 92b is a metal elastic member substantially U-shaped in cross section and configured to press the second housing 51b through the securing fitting 90. The same components in the first U-spring 92a and the second U-spring 92b, which are of the same shape, are denoted by the same reference numerals. The first U-spring 92a and the second U-spring 92b are collectively referred to as U-springs 92. As illustrated in FIG. 5 and FIG. 7, each U-spring 92 is in contact with the inner periphery of the metal tube 95 at end portions 93 and 94 which are both ends of the U-shape. The end portions 93 and 94 are curved at their extremities, and formed as curved contact portions which are in contact with the inner periphery of the metal tube 95 at the curved surfaces. Each curved surface in contact with the inner periphery of the metal tube 95 is formed such that the curvature radius thereof is smaller than or equal to that of the contact portion of the inner periphery of the metal tube 95. For example, as illustrated in an enlarged view in FIG. 7, the curvature radius of a curved surface 93a of the end portion 93 of the second U-spring 92b in contact with the inner periphery of the metal tube 95 is smaller than that of a curved surface 95a of the inner periphery of the metal tube 95 in contact with the end portion 93. The curvature radius of the curved surface of each of the end portions 93 and 94 of the U-springs 92 in contact with the metal tube 95 is not limited to a specific value, but is, for example, in the range of 0.3 mm to 5.1 mm. The U-springs 92 press the first housing 51a and the second housing 51b through the securing fitting 90 to bring the first housing 51a and the second housing 51b closer to each other, with the sensor element 20 interposed therebetween, with an elastic force generated when the end portions 93 and 94 are pressed by the metal tube 95.

The metal tube 95 is a cylindrical member that is in contact with the first U-spring 92a and the second U-spring 92b and is around the first housing 51a and the second housing 51b. The metal tube 95 is positioned such that the central axis thereof is along the length of the sensor element 20. The metal tube 95 causes the U-springs 92 to generate an elastic force, as described above, by allowing the inner periphery thereof to press the end portions 93 and 94 of the U-springs 92. As illustrated in FIG. 5 and FIG. 7, the metal tube 95 is provided with eight protrusions 96 on the outer periphery thereof and is also provided with eight grooves 97 in the inner periphery thereof. The protrusions 96 are spaced at 45° intervals, and the grooves 97 are positioned opposite the respective protrusions 96. The protrusions 96 and the grooves 97 are formed in the process of crimping the metal tube 95. The crimping process will be described later on. The end portions 93 and 94 are positioned off the grooves 97. The metal tube 95 has a small-diameter portion 98 (see FIG. 6 and FIG. 9) at an end adjacent to the base end of the sensor element 20. The small-diameter portion 98 has an inside diameter smaller than that of The other part of the metal tube 95. The small-diameter portion 98 prevents relative displacement of the U-springs 92 in the rightward direction in FIG. 6. The dimensions of the metal tube 95 are not particularly limited. For example, the radius of the inner periphery of the metal tube 95 is 4 mm to 8 mm (see FIG. 9) and the thickness of the metal tube 95 is 0.4 mm to 1.0 mm (see FIG. 9). A larger thickness is preferable, because the larger the thickness, the less likely the metal tube 95 will be loosened (i.e., the less likely the force of pressing the U-springs 92 will decrease). For example, SUS430 can be used as a material of the metal tube 95. The metal tube 95 having a lower thermal expansion coefficient is preferable. This is because the lower the thermal expansion coefficient, the more it is possible to prevent loosening of the U-springs 92 caused by thermal expansion of the metal tube 95, and thus to prevent the elastic force for pressing the housings 51 from decreasing. The metal tube 95 is formed such that the arithmetical mean roughness Ra of the inner periphery thereof is 1 μm or less (preferably 0.8 μm or less).

The securing fitting 90 is formed by bending a metal plate into a substantially C-shape in cross section. The securing fitting 90 has an elastic force with which the first housing 51a and the second housing 51b can be clamped and pressed closer to each other. With this elastic force and the elastic force of the U-springs 92 described above, the securing fitting 90 clamps the first housing 51a and the second housing 51b. The first housing 51a and the second housing 51b clamp the sensor element 20, with the supporting portions 71b and the conducting portions 71c of the contact fittings 71 facing the front-surface electrodes 21a or the back-surface electrodes 21b of the sensor element 20. Thus, the supporting portions 71b and the conducting portions 71c are elastically deformed by the pressing force of the securing fitting 90 to clamp and secure the sensor element 20. Since the supporting portions 71b and the conducting portions 71c are elastically deformed, the sensor element 20 can be reliably clamped and secured by the resulting pressing force. Also, since the supporting portions 71b and the conducting portions 71c are elastically deformed, it is possible to reliably maintain the electrical contact between the supporting portions 71b and the electrodes 21 and the electrical contact between the conducting portions 71c and the electrodes 21.

The material of the supporting portions 71b and the conducting portions 71c and how the supporting portions 71b and the conducting portions 71c are to be bent are determined such that the supporting portions 71b and the conducting portions 71c are not plastically deformed at, or within a predetermined margin of, the pressing force of the the securing fitting 90 and the U-springs 92. The spring constant of each of the supporting portion 71b and the conducting portion 71c is preferably in the range of 500 N/mm to 4000 N/mm. This spring constant is a spring constant in a direction (Z direction) orthogonal to a line tangent to the tip of each of the supporting portion 71b and the conducting portion 71c assembled to each housing 51. With this spring constant, the above-described effects can be more reliably achieved. For example, since the supporting portions 71b and the conducting portions 71c are not subjected to any load and not displaced immediately after production of the contact fittings 71, both displacement and load are zero (corresponding to the origin of the graph) as illustrated in FIG. 10. On the other hand, when the sensor element 20 is assembled to the connector 50, the supporting portions 71b and the conducting portions 71c are subjected to load and compressed in the Z direction. Therefore, the displacement increases as the load increases. The displacement changes along a straight line A (corresponding to a spring constant of 500 N/mm) in FIG. 10. After assembly of the sensor element 20 to the connector 50, the load is 50 N and the displacement is 100 μm. Then, if the load decreases in the range of 0 N to 50 N, the displacement decreases as indicated by a downward arrow along the straight line A, whereas if the load increases, the displacement increases as indicated by an upward arrow along the straight line A. By appropriately determining the material of the supporting portions 71b and the conducting portions 71c and how the supporting portions 71b and the conducting portions 71c are to be bent, it is possible to realize the initial relationship between load and displacement indicated by the straight line A, and the relationship between load and displacement after the assembly also indicated by the straight line A. The material etc. may be determined such that, after the sensor element 20 is assembled to the connector 50 and the load and the displacement reach 50 N and 100 μm, respectably, if the load decreases in the range of 0 N to 50 N, the displacement decreases as indicated by a downward arrow along a straight line B (corresponding to a spring constant of 1000 N/mm), whereas if the load increases, the displacement increases as indicated by an upward arrow along the straight line B. Alternatively, the material etc. may be determined such that, after the sensor element 20 is assembled to the connector 50 and the load and the displacement reach 100 N and 200 μm, respectably, if the load decreases in the range of 0 N to 100 N, the displacement decreases as indicated by a downward arrow along a straight line C (corresponding to a spring constant of 4000 N/mm), whereas if the load increases, the displacement increases as indicated by an upward arrow along the straight line C. Thus, as described above, the spring constant of each of the supporting portion 71b and the conducting portion 71c after assembly of the sensor element 20 to the connector 50 can be set to be in the range of 500 N/mm to 4000 N/mm.

The conditions of the sensor element 20 and the connector 50 of the gas sensor 10 during vibration will now be described with reference to FIG. 11. When the U-springs 92 are at positions indicated by solid lines in FIG. 11, if vibration is applied to the gas sensor 10 and an upward force in FIG. 11 acts on the connector 50, the U-springs 92 are deformed as indicated by broken lines in the drawing. Specifically, the end portions 93 and 94 of the first U-spring 92a slide along the inner periphery of the metal tube 95 to be displaced closer to each other, so that the vibration is absorbed by the elastic function of the first U-spring 92a. Similarly, if a downward force in FIG. 11 acts on the connector 50, the end portions 93 and 94 of the second U-spring 92b slide along the inner periphery of the metal tube 95 to be displaced closer to each other, so that the vibration is absorbed by the elastic function of the second U-spring 92b. In the gas sensor 10 of the present embodiment, where the arithmetical mean roughness Ra of the inner periphery of the metal tube 95 is 1 μm or less and the end portions 93 and 94 of the U-springs 92 are formed as curved contact portions, the end portions 93 and 94 of the U-springs 92 can slide smoothly along the inner periphery of the metal tube 95 and vibration can be absorbed. Therefore, defective contact between the contact fittings 71 and the sensor element 20 and wear and cracks in the sensor element 20 are less likely to occur. If the end portions 93 and 94 of the U-springs 92 are caught and stuck in the inner periphery of the metal tube 95, the U-springs 92 cannot be deformed as indicated by the broken lines, and hence vibration cannot be absorbed by the U-springs 92. In this case, since a force caused by vibration is applied to contact points between the sensor element 20 and the contact fittings 71, defective contact between the contact fittings 71 and the sensor element 20 and wear and cracks in the sensor element 20 are more likely to occur. The gas sensor 10 of the present embodiment can prevent this and is resistant to vibration. As described above, the end portions 93 and 94 of the U-springs 92 are positioned off the grooves 97 of the metal tube 95. Even if the end portions 93 and 94 are brought closer to or away from each other and displaced by vibration, they do not reach the positions of the grooves 97. For this, for example, the material and shape of the U-springs 92 and the positions of the grooves 97 may be determined such that, within a range of possible vibrations applied to the gas sensor 10, the regions where the end portions 93 and 94 of the U-springs 92 are displaced do not overlap with the grooves 97.

A method for making the gas sensor 10 will now be described. First, a method for making the contact fittings 71 will be described. Each of the contact fittings 71 is formed by die-cutting and bending a metal plate. As illustrated in FIG. 12, first, a metal plate is die-cut into a shape having a metal plate portion 100 of substantially rectangular shape and a metal piece 110 connecting to a long side of the metal plate portion 100. Next, the tip portion 71a and the connecting portion 71f illustrated in FIG. 13 are formed by bending a region 100a and a region 100f, respectively, of the metal plate portion 100 upward from the horizontal plane of FIG. 12. Also, the supporting portion 71b and the conducting portion 71c illustrated in FIG. 13 are formed by bending a region 100b and a region 100c, respectively, of the metal plane portion 100 downward from the horizontal plane of FIG. 12. The upright portion 71d is formed by folding a region 111 of the metal piece 110 along a straight line 111a upward 90° from the horizontal plane of FIG. 12, and folding a region 112 of the metal piece 110 along a straight line 112a. The hook 71e is formed by bending a region 113. In the process described above, the contact fitting 71 of three-dimensional shape can be easily made from a metal sheet. As illustrated in FIG. 12 and FIG. 13, the metal plate portion 100 is provided with cutouts 101 having a depth greater than or equal to the thickness of the region 111. Thus, when the region 111 is folded along the straight line 111a, the region 111 can be accommodated within a region directly above a front surface 102 of the metal plate portion 100. The widths of the regions 112 and 113 are determined such that the regions 112 and 113 can also be accommodated within the region directly above the front surface 102 of the metal plate portion 100. Since the hook 71e is formed by bending The region 113 along the length of the metal plate portion 100 toward the connecting portion 71f, the entire upright portion 71d is also accommodated within the region directly above the front surface 102 of the metal plate portion 100. When the upright portions 71d of the plurality of contact fittings 71 are formed into the above-described shape, it is possible to reduce the arrangement width of the contact fittings 71 arranged in a direction orthogonal to the length of the contact fittings 71, and thus to reduce the size of the housings 51. This means that the size of the connector 50 can be reduced. Moreover, since the connector 50 and the sensor element 20 communicate with each other through the contact fittings 71 which are elastic bodies, vibration transmitted from the outer cylinder 46, through the rubber stopper 47, to the lead wires 45, and to the connector 50 is not directly transmitted to the sensor element 20. For example, if the connector 50 and the sensor element 20 communicate with each other through non-elastic protrusions of contact fittings, vibration transmitted from the outer cylinder 46, through the rubber stopper 47, to the lead wires 45, and to the connector 50 is directly transmitted to the sensor element 20. Moreover, if the gas sensor 10 is installed in a vibrating environment such as in a vehicle, the sensor element 20 and the connector 50 vibrate, as described above, with respect to the upper end portion P illustrated in FIG. 1. In such a case, if the contact fittings 71 do not have an elastic force, the lead wires 45, the rubber stopper 47, and the outer cylinder 46, as well as the connector 50, are included in the vibrating system of the sensor element 20. This raises a concern about the occurrence of excessive repeated stress with respect to the upper end portion P described above. However, such a concern can be effectively resolved in the present embodiment, where the contact fittings 71 being elastic bodies allow communication between the connector 50 and the sensor element 20. Additionally, since moment generated in the connector 50 by vibration can be reduced as the size or weight of the connector 50 decreases, the repeated stress on the sensor element 20 caused by moment of the connector 50 can be reduced. Thus, the life of the sensor element 20 can be extended. Moreover, since moment generated in the connector 50 can be reduced, it is possible to make the connector 50 more resistant to vibration and extend the life of the connector 50.

A method for making the connector 50 will now be described with reference to FIG. 14 to FIG. 16. FIG. 14 and FIG. 15 are perspective views schematically illustrating a process of making the connector 50. First, the second housing 51b is prepared (FIG. 14(a)), and four contact fittings 71 are arranged on the second housing 51b in a direction orthogonal to the length of the contact fittings 71 and held by the second housing 51b (FIG. 14(b)). Next, a primary assembly is prepared which includes the sensor element 20, the main fitting 41, the protective cover 30, the inner cylinder 42, the ceramic supporters 43a to 43c, and the ceramic powder 44a and 44b illustrated in FIG. 1. The primary assembly is assembled, for example, in the following manner. First, after the inner cylinder 42 is welded into the main fitting 41, the plurality of ceramic supporters 43a to 43c and the ceramic powder 44a and 44b are placed inside the inner cylinder 42 and the main fitting 41, with the sensor element 20 inserted in the inner cylinder 42 and the main fitting 41. Next, the inner protective cover 31 and the outer protective cover 32 are welded to the main fitting 41 to form the protective cover 30 and thus, the primary assembly is produced. Then, the sensor element 20 of the primary assembly is placed on the second housing 51b such that the back-surface electrodes 21b of the sensor element 20 are electrically connected to the supporting portions 71b and the conducting portions 71c of the contact fittings 71 (FIG. 14(c)). Note that the illustration of all the components of the primary assembly, except the sensor element 20, is omitted in FIG. 14(c). Next, in the same manner as that illustrated in FIG. 14(b), four contact fittings 71 are arranged on the first housing 51a in a direction orthogonal to the length of the contact fittings 71 and held by the first housing 51a. Then, the sensor element 20 is clamped between the first housing 51a and the second housing 51b (FIG. 15(a)). Thus, the front-surface electrodes 21a of the sensor element 20 face and are electrically connected to the respective contact fittings 71 at the supporting portions 71b and the conducting portions 71c. Here, the connecting portions 71f of the contact fittings 71 are connected to the lead wires 45 that pass through the inside of the rubber stopper 47.

Next, the securing fitting 90 is formed by bending a metal plate into a substantially C-shape in cross section. Then, an open portion of the securing fitting 90 is temporarily widened for insertion of the first housing 51a and the second housing 51b thereinto (FIG. 15(b)). Thus, the securing fitting 90 presses the first housing 51a and the second housing 51b closer to each other and secures them. Then, the first U-spring 92a and the second U-spring 92b are attached to clamp the securing fitting 90 and the housings 51 therebetween (FIG. 15(c)). The first U-spring 92a and the second U-spring 92b can be formed by bending a metal plate into a U-shape. The end portions 93 and 94 of the U-shape of each of the first U-spring 92a and the second U-spring 92b are bent to serve as curved contact portions, each having a curved surface with a predetermined radius. The U-springs 92 are attached such that the end portions 93 and 94 are directed opposite the housings 51. The U-springs 92 may be attached to the securing fitting 90 in advance. Next, the cylindrical metal tube 95 having an inner periphery with an arithmetical mean roughness Ra of 1 μm or less is prepared. The metal tube 95 is positioned such that it is located around the housings 51 and the U-springs 92 and that the central axis thereof is along the length of the sensor element 20 (FIG. 16(a)). Thus, the first U-spring 92a is located between the metal tube 95 and the first housing 51a, and the second U-spring 92a is located between the metal tube 95 and the second housing 51b. The inner periphery of the metal tube 95 can be made to have an arithmetical mean roughness Ra of 1 μm or less, for example, by ironing in which steel small balls with a radius slightly larger than that of the inner periphery of the metal tube 95 are passed through, barrel finishing, or shot peening.

Figure 17:
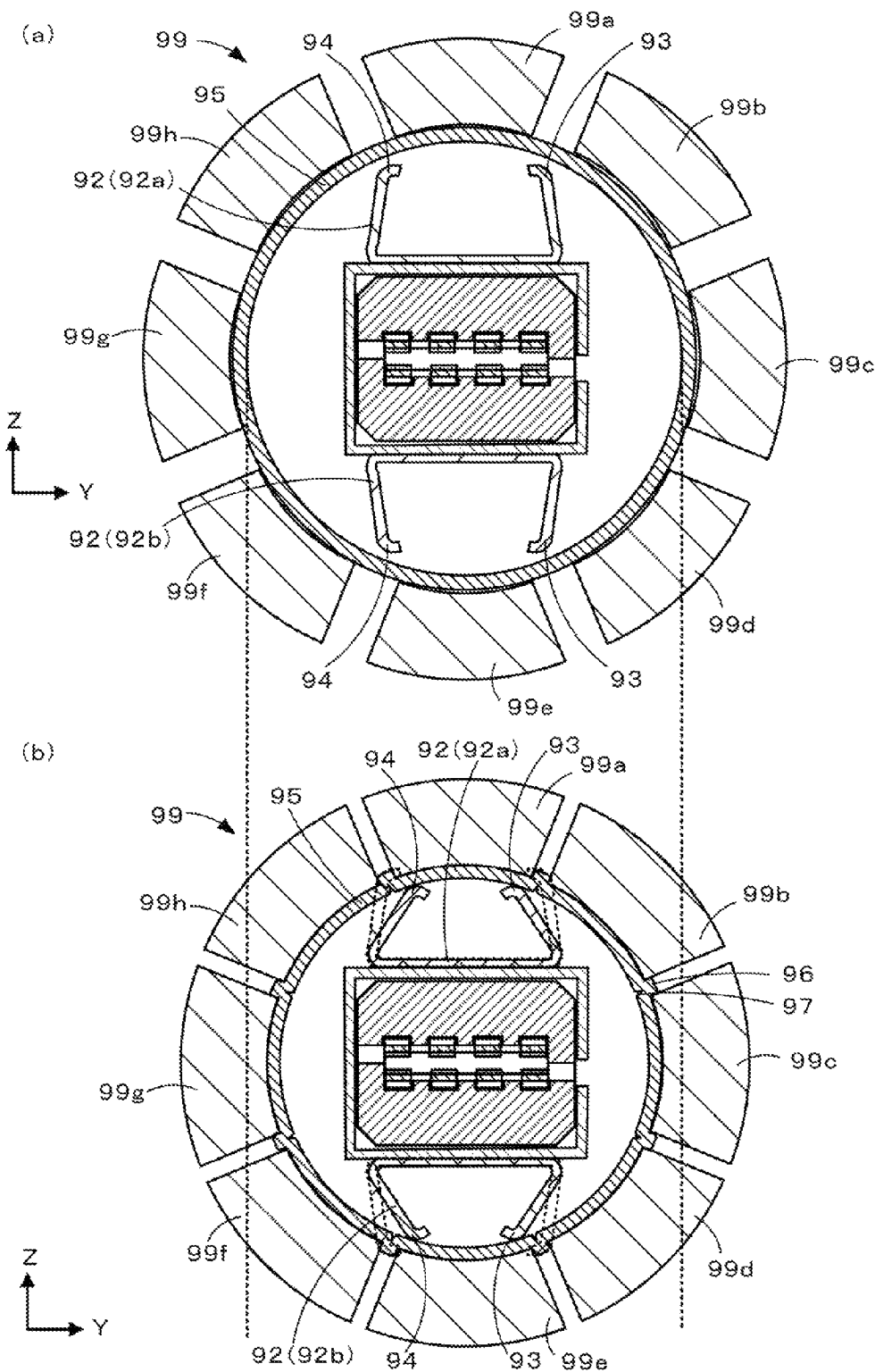
FIG. 17 illustrates how the metal tube 95 is crimped.

After the metal tube 95 and the U-springs 92 are placed, the outer periphery of the metal tube 95 is crimped to reduce the inside diameter of the metal tube 95 (FIG. 16(b)). This crimping process is illustrated in FIG. 17. First, as illustrated in FIG. 17(a), a crimping jig 99 is placed around the metal tube 95 before crimping. The crimping jig 99 is made by cutting a cylindrical member having a diameter larger than that of the metal tube 95 into eight parts 99a to 99h of 45° each. The metal tube 95 is surrounded by the parts 99a to 99h, which are pressed inward from the outer periphery of the crimping jig 99 (i.e., in the direction toward the center of the circle of the metal tube 95). Thus, the outer periphery of the metal tube 95 is crimped to reduce the inside diameter of the metal tube 95 (FIG. 17(b)). The parts 99a to 99h are pressed from the outer periphery of the crimping jig 99, for example, by inserting and axially press-fitting the crimping jig 99 and the metal tube 95 into a hollow conical member which axially gradually reduces its inside diameter. In this crimping process, the protrusions 96 and the grooves 97 of the metal tube 95 are formed at positions corresponding to respective gaps between adjacent ones of the parts 99a to 99h. Therefore, in this crimping process, the parts 99a to 99h are placed such that the end portions 93 and 94 can be located off the grooves 97. The number and shape of the parts 99a to 99h are not limited to those illustrated in FIG. 17. For example, the parts 99a to 99h illustrated in FIG. 17 are of identical shape, because they are obtained by evenly cutting a cylindrical member into segments of 45° each. However, such a cylindrical member may not be cut into equal segments, but may be cut into segments of different shapes.

When the crimping process is performed as described above, the inner periphery of the metal tube 95 is brought into contact with and presses the curved surfaces of the end portions 93 and 94 of the U-springs 92, which generate an elastic force. With this elastic force, the first U-spring 92a presses the first housing 51a closer to the second housing 51b, with the sensor element 20 interposed therebetween. Similarly, the second U-spring 92b presses the second housing 51b closer to the first housing 51a, with the sensor element 20 interposed therebetween. Thus, the sensor element 20 is clamped between the housings 51. The extent to which the inside diameter of the metal tube 95 is to be reduced may be determined by an experiment, on the basis of the resulting inside diameter and the elastic force required for the U-springs 92. The curvature radius of each of the curved surfaces of the end portions 93 and 94 of the U-springs in contact with the inner periphery of the metal tube 95 is set to a value determined in advance such that it is smaller than or equal to a curvature radius of the inner periphery (equivalent to the radius of the inner periphery in the present embodiment) of the crimped metal tube 95. After the crimping process, only an end portion of the metal tube 95 adjacent to the base end of the sensor element 20 is pressed inward to form the small-diameter portion 98. The connector 50 described above is thus obtained.

After the connector 50 that clamps the sensor element 20 of the primary assembly is produced as described above, the outer cylinder 46 is welded to the main fitting 41 to obtain the gas sensor 10 illustrated in FIG. 1.

The gas sensor 10 can realize the above-described effect which provides better sliding between the inner periphery of the metal tube 95 and the end portions 93 and 94 of the U-springs 92b and allows absorption of vibration. Since the end portions 93 and 94 of the U-springs 92b slide smoothly along the inner periphery of the metal tube 95, the end portions 93 and 94 of the U-springs 92 can be prevented from being caught in the inner periphery of the metal tube 95 and unevenly deformed in the process of crimping the outer periphery of the metal tube 95. Thus, since it is possible to prevent uneven contact between the sensor element 20 and the contact fittings 71 caused by a biased elastic force of the U-springs 92, poor contact between the sensor element 20 and the contact fittings 71 during vibration is less likely to occur. The gas sensor 10 resistant to vibration can thus be obtained.

The correspondence between components of the present embodiment and components of the present invention will now be described. The sensor element 20 of the present embodiment corresponds to a sensor element of the present invention. The contact fittings 71 of the present embodiment correspond to a first contact fitting and a second contact fitting of the present invention. The first housing 51a of the present embodiment corresponds to a first housing of the present invention. The second housing 51b of the present embodiment corresponds to a second housing of the present invention. The metal tube 95 of the present embodiment corresponds to a metal tube of the present invention. The first U-spring 92a of the present embodiment corresponds to a first elastic member of the present invention. The second U-spring 92b of the present embodiment corresponds to a second elastic member of the present invention. The securing fitting 90 of the present embodiment corresponds to a third elastic member of the present invention.

It is to be understood that the present invention is not limited to the embodiments described above, and can be realized in various forms within the technical scope of the present invention.

For example, in the embodiments described above, better sliding of the U-springs 92 along the inner periphery of the metal tube 95 is achieved by setting the arithmetical mean roughness Ra of the inner periphery of the metal tube 95 to 1 μm or less. However, the inner periphery of the metal tube 95 may be plated or coated with fluororesin, liquid lubricant, or solid lubricant. Alternatively, the curved surfaces of both the end portions 33 and 34 of each of the U-springs 92 in contact with the inner periphery of the metal tube 95 may be plated or coated with fluororesin, liquid lubricant, or solid lubricant. With this, it is still possible to provide better sliding of the U-springs 92 along the inner periphery of the metal tube 95 and realize a gas sensor resistant to vibration. When plating or the like is applied as described above, the arithmetical mean roughness Ra of the inner periphery of the metal tube 95 may be 1 μm or less, or may be larger than 1 μm. Examples of the plating include silver plating. The thickness of the plating is not particularly limited but is, for example, 1 μm to 2 μm. Examples of the liquid lubricant include high-purity refined oil, such as press oil (e.g., Aqua Press MA-10R produced by Aqua Chemical Co., Ltd.). Examples of the solid lubricant include molybdenum disulfide.

In the embodiments described above, the end portions 93 and 94, which are both ends of each of the U-springs 92, are formed as curved contact portions. Alternatively, only one of the end portions 93 and 94 may be formed as a curved contact portion. However, for better sliding between the U-springs 92 and the inner periphery of the metal tube 95, it is preferable that both the end portions 93 and 94 be formed as curved contact portions.

Although the first housing 51a and the second housing 51b each have the regulating members 56 and 57 in the embodiments described above, the regulating members 56 and 57 may be separate from the first housing 51a and the second housing 51b. Alternatively, each of the first housing 51a and the second housing 51b may have regulating members in both sides thereof, so that the distance between the first housing 51a and the second housing 51b is fixed by contact between their opposite regulating members.

Although both the supporting portions 71b and the conducting portions 71c are configured to clamp the sensor element 20 with pressing force in the embodiments described above, the supporting portions 71b may not be provided. However, as described above, if the conducting portions 71c are located on a side of the through holes 21e adjacent to the base end of the sensor element 20, the pressing force from the conducting portions 71c may act on the through holes 21e and cause cracks in the sensor element 20. To prevent this, it is preferable that the sensor element 20 be clamped also by the supporting portions 71b.

Although the hooks 71e bend toward the connecting portions 71f in the embodiments described above, they may bend in the opposite direction. In the latter case, the retainer 54 in each insertion hole 53 may be formed on the opposite side in the insertion hole 53. The upright portions 71d of the contact fittings 71 may be formed by any folding and bending process, as long as each of the upright portions 71d is accommodated within a region directly above the front surface 102 of the metal plate portion 100.

In the embodiments described above, by crimping the outer periphery of the metal tube 95 to reduce the inside diameter of the metal tube 95 as illustrated in FIG. 17, the inner periphery of the metal tube 95 is brought into contact with and presses the curved surfaces of the end portions 93 and 94 of the U-springs 92, which thus generate an elastic force. However, any process may be performed as long as the metal tube 95 is inwardly pressed and plastically deformed to allow the U-springs 92 to generate an elastic force. For example, as illustrated in FIG. 18, the metal tube 95 may be pressed and plastically deformed to bring the first U-spring 92a and the second U-spring 92b illustrated in FIG. 18(a) closer to each other (in the vertical direction in the drawing), so that the metal tube 95 is deformed into an oval shape as illustrated in FIG. 18(b) to allow the U-springs 92 to generate an elastic force. Since the protrusions 96 and the grooves 97 are not created in this process, there is no need to take into account the positional relationship between the grooves 97 and the end portions 93 and 94 of the U-springs 92.

EXAMPLES

Examples 1 to 11, Comparative Example 1

The gas sensors 10 according to Examples 1 to 11 and Comparative Example 1 were made by the above-described method for making the gas sensor 10. The gas sensors according to Examples 1 to 11 and Comparative Example 1 are different, as shown in Table 1, in terms of the arithmetical mean roughness Ra of the inner periphery of the metal tube 95 and whether plating or the like was performed before the crimping process described above. Note that when ironing was performed, the corresponding arithmetical mean roughness Ra in Table 1 indicates a value measured after the ironing. When a process other than ironing, such as plating, was performed, the corresponding arithmetical mean roughness Ra indicates a value measured before the process. The configurations and methods for making the gas sensors according to Examples 1 to 11 and Comparative Example 1 are the same, except for those shown in Table 1. Specifically, in Examples 1 to 11 and Comparative Example 1, the U-springs 92 made of SUS301 and the metal tube 95 made of SUS430 were used, the curvature radius of each curved surface of the end portions 93 and 94 of the U-springs 92 in contact with the metal tube 95 was 0.5 mm, and the radius of the inner periphery of the metal tube 95 was 5.9 mm before crimping and 5.2 mm after crimping.

TABLE 1

| | | Condition of inner periphery of metal tube | | |
|---|---|---|---|---|
| | | Arithmetical mean roughness Ra (μm) | Ironing | Process other than ironing |
| Example | 1 | 1.0 | Performed | Not performed |
| | 2 | 0.9 | Performed | Not performed |
| | 3 | 0.8 | Performed | Not performed |
| | 4 | 1.2 | Not performed | Plating (Silver) |
| | 5 | 1.2 | Not performed | Coating (Fluororesin) |
| | 6 | 1.2 | Not performed | Coated with solid lubricant (Molybdenum disulfide) |

TABLE 1-continued

| | | Condition of inner periphery of metal tube | |
|---|---|---|---|
| | Arithmetical mean roughness Ra (μm) | Ironing | Process other than ironing |
| 7 | 1.2 | Not performed | Coated with lubricant oil |
| 8 | 1.0 | Performed | Plating (Silver) |
| 9 | 1.0 | Performed | Coating (Fluororesin) |
| 10 | 1.0 | Performed | Coated with solid lubricant (Molybdenum disulfide) |
| 11 | 1.0 | Performed | Coated with lubricant oil |
| Comparative Example 1 | 1.2 | Not performed | Not performed |

(Evaluation 1)

Figure 19:
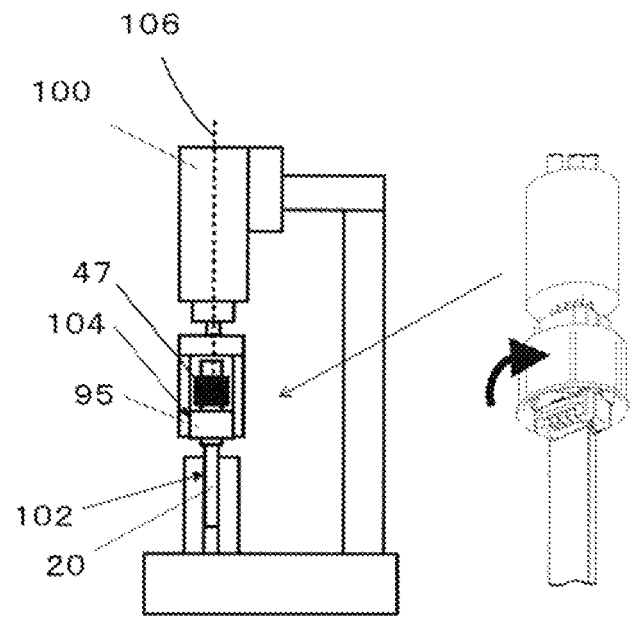
FIG. 19 illustrates a torque measurement.
Figure 19:
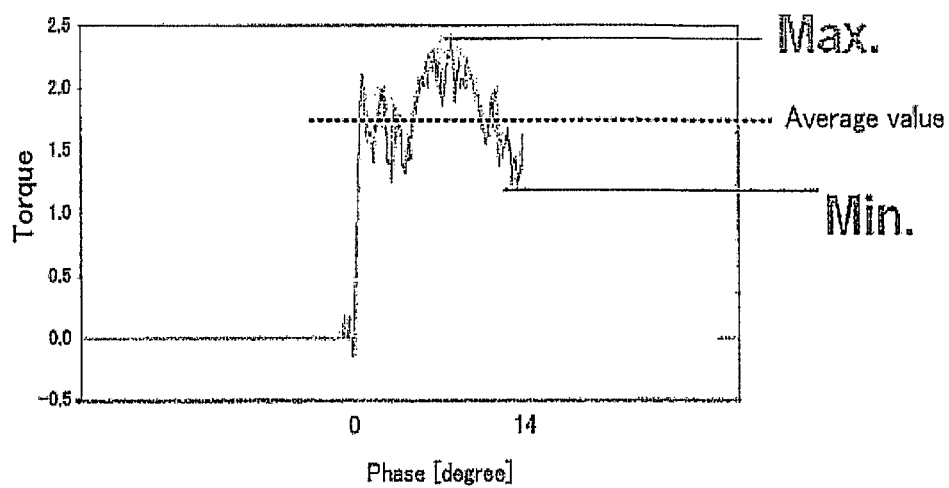
Figure 20:
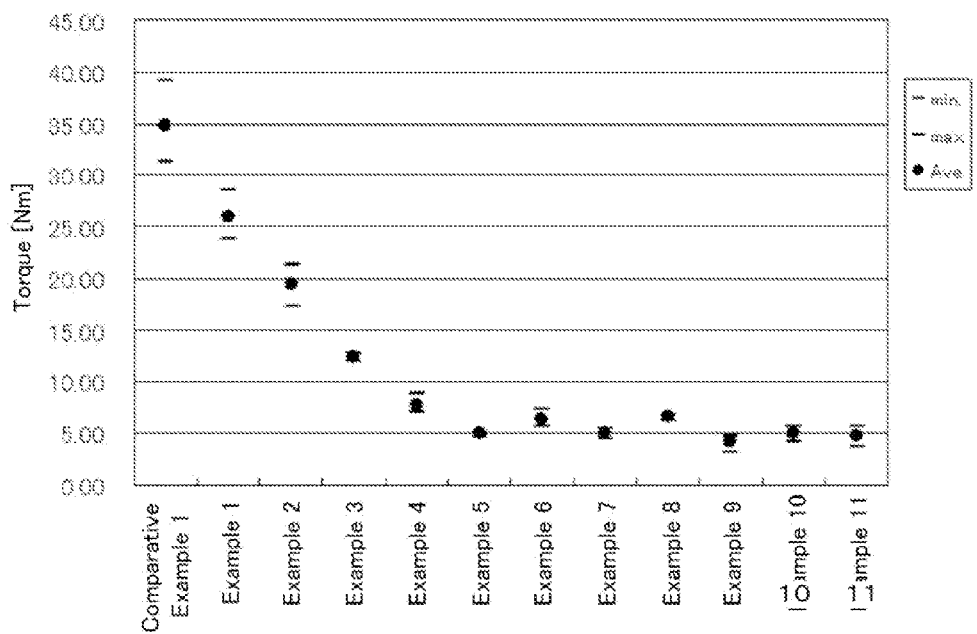
FIG. 20 is a graph showing a maximum value, a minimum value, and an average value of torque waveform.

For each of the gas sensors 10 prepared for Examples 1 to 11 and Comparative Example 1, torque generated when the metal tube 95 was rotated was measured by a torque meter 100 (NX500-TU produced by Nitto Seiko Co., Ltd.). FIG. 19 illustrates a torque measurement. Torque was measured in the following manner. First, as illustrated in FIG. 19(a), only the sensor element 20, the connector 50, the lead wires 45, and the rubber stopper 47 (collectively referred to as a preliminary group) were taken out from the gas sensor 10 and secured by clamping the sensor element 20 with a securing member 102 of the torque meter 100. When the metal tube 95 was rotated about a rotation axis 106 at a rotation speed of about 20 rpm (from a phase of 0° to 14°) while being gripped by a gripping member 104, a waveform of torque acting on the rotation axis 106 was measured. Then, a maximum value, a minimum value, and an average value of torque waveform measured as illustrated in FIG. 19(b) were calculated. The result is shown in FIG. 20. The toque was measured during rotation from a phase of 0° to 14° as described above. This is because if the end portions 93 and 94 of the U-springs 92 are moved to reach the grooves 97 by rotation, torque different from that generated during use of the gas sensor 10 is generated and hence a proper measurement cannot be made. The grooves 97 of the gas sensor 10 are arranged at 45° intervals, and the maximum rotation angle up to which the end portions 93 and 94 of the U-springs 92 can be moved by rotation without reaching the grooves 97 is 14° (or 7° in both left and right directions in FIG. 7). Therefore, the toque was measured during rotation from 0° to 14° as described above. For the torque measurement, three gas sensors 10 were prepared for each of Examples 1 to 11 and Comparative Example 1. Then, a maximum value, a minimum value, and an average value of torque waveforms for the three gas sensors 10 were calculated. For example, a maximum value and a minimum value of torque waveform for Example 1 shown in FIG. 20 represent maximum and minimum instantaneous values of three torque waveforms measured for the three gas sensors 10 prepared for Example 1. Also, an average value of torque waveform for Example 1 shown in FIG. 20 represents an average torque value of the three torque waveforms.

As can be seen from FIG. 20, torque values for Examples 1 to 11 are smaller than that for Comparative Example 1. This shows that sliding between the inner periphery of the metal tube 95 and the U-springs 92 of each of the gas sensors 10 for Examples 1 to 11 is better than that for Comparative Example 1. The results of measurements for Examples 1 to 3 show that the smaller the arithmetical mean roughness Ra of the inner periphery of the metal tube 95, the better the sliding between the inner periphery of the metal tube 95 and the U-springs 92. The results of measurements for Comparative Example 1 and Examples 4 to 6 show that even when the gas sensors 10 are the same in terms of the arithmetical mean roughness Ra of the inner periphery of the metal tube 95, the sliding between the inner periphery of the metal tube 95 and the U-springs 92 is better if the inner periphery is plated or processed in other ways. The results of measurements for Examples 8 to 11 show that if not only setting the arithmetical mean roughness Ra of the inner periphery of the metal tube 95 to 1 μm or less, but also applying plating or the like to the inner periphery, the sliding between the inner periphery of the metal tube 95 and the U-springs 92 is better than that in the case where only one of them is performed.

Figure 21:
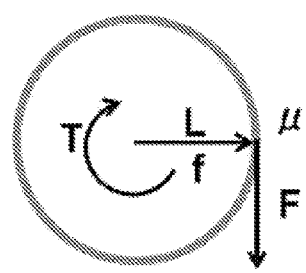
FIG. 21 illustrates variables used in calculating a coefficient of kinetic friction μ.
Figure 22:
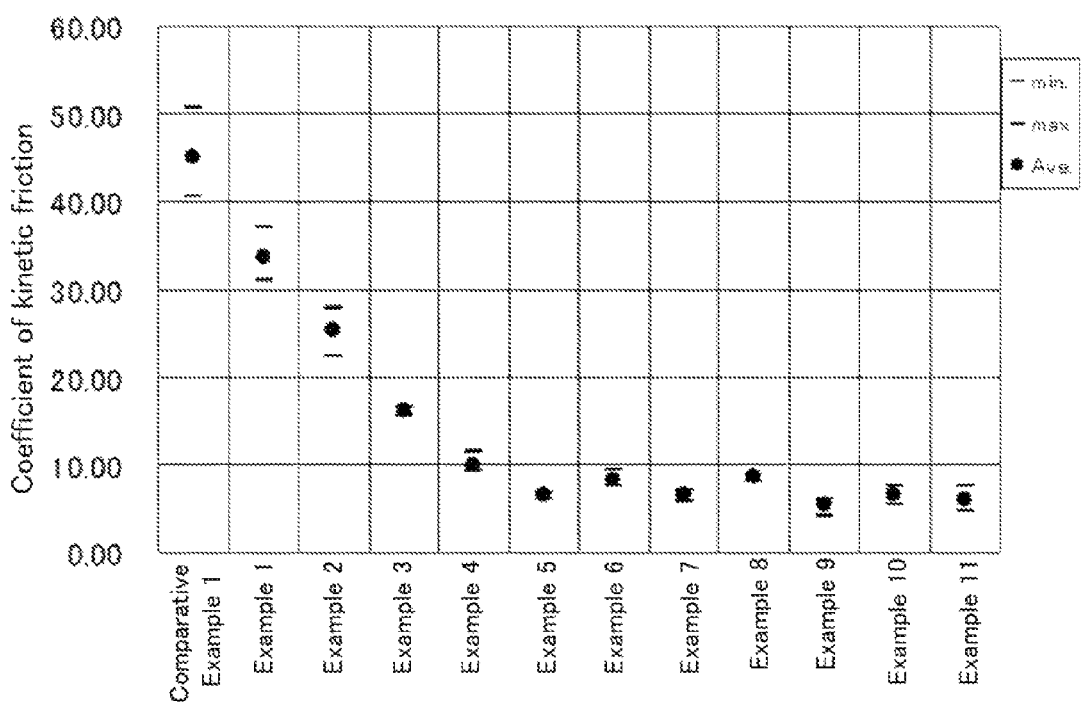
FIG. 22 is a graph showing a maximum value, a minimum value, and an average value of a coefficient of kinetic friction μ calculated from torque.

As a value indicating smoothness of sliding between the inner periphery of the metal tube 95 and each U-spring 92, a coefficient of kinetic friction between the inner periphery of the metal tube 95 and the U-spring 92 can be calculated from the torque shown in FIG. 20. FIG. 21 illustrates variables used in this calculation. The following equations (1) and (2) can be obtained, where, as illustrated in FIG. 21, T (N·m) represents torque generated when the metal tube 95 is rotated, L (m) represents a radius of the inner periphery of the metal tube 95, μ represents a coefficient of kinetic friction between the inner periphery of the metal tube 95 and each U-spring 92, F (N) represents a tangential force that rotates the metal tube 95, and f (N) represents a force with which the U-spring 92 radially presses the metal tube 95 (i.e., the sum of pressing forces at both ends of one of the U-springs 92). The following equation (3) can be derived from the equations (1) and (2). In the present embodiment, the radius L of the inner periphery of the metal tube 95 crimped as described above is 0.0052 m. The pressing force f applied by the U-spring 92 after crimping measured 250 N. Thus, by using these values and the value of torque T shown in FIG. 20, the coefficient of kinetic friction μ between the inner periphery of the metal tube 95 and the U-spring 92 was calculated. The result is shown in FIG. 22. As can been seen from the coefficient of kinetic friction μ for Example 1 in FIG. 22, setting the arithmetical mean roughness Ra of the inner periphery of the metal tube 95 to 1 μm or less is equivalent to setting the coefficient of kinetic friction μ between the inner periphery of the metal tube 95 and the U-spring 92 to 37.10 or less. Similarly, setting the arithmetical mean roughness Ra of the inner periphery of the metal tube 95 to 0.8 μm or less is equivalent to setting the coefficient of kinetic friction μ between the inner periphery of the metal tube 95 and the U-spring 92 to 16.61 or less. Although the coefficient of kinetic friction μ was calculated as a value obtained after crimping, the coefficient of kinetic friction μ is a constant value which does not change before and after crimping.

$$T = L \times F \quad (1)$$

$$\mu = F/f \quad (2)$$

$$\mu = T/f/L \quad (3)$$

(Evaluation 2)

Figure 24:
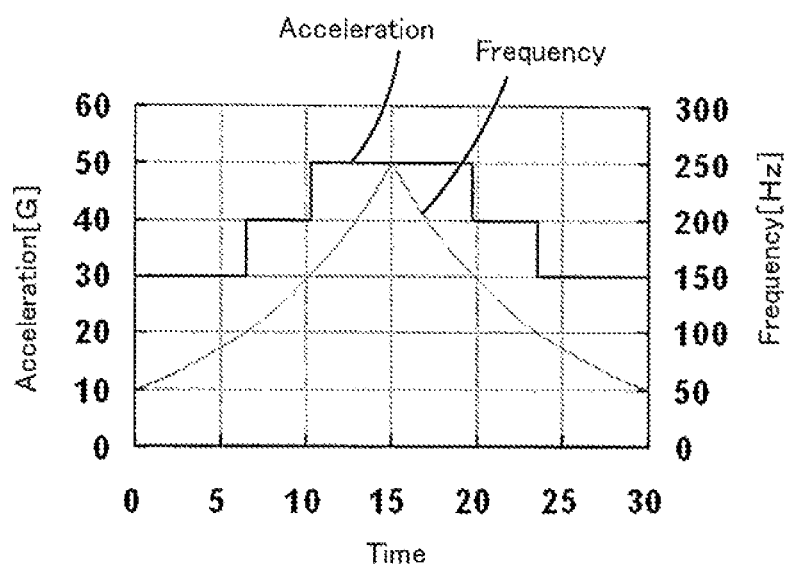
FIG. 24 illustrates vibration conditions for a heat vibration test.
Figure 25:
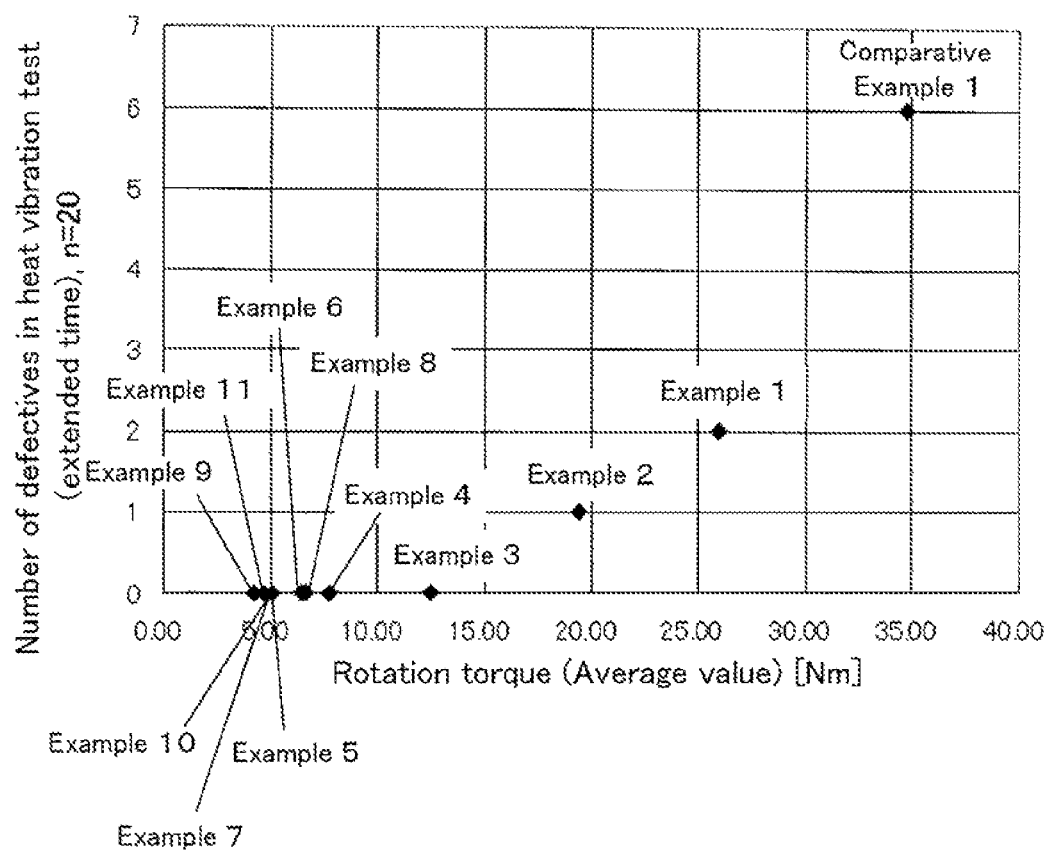
FIG. 25 illustrates a result of a heat vibration test.
Figure 26:
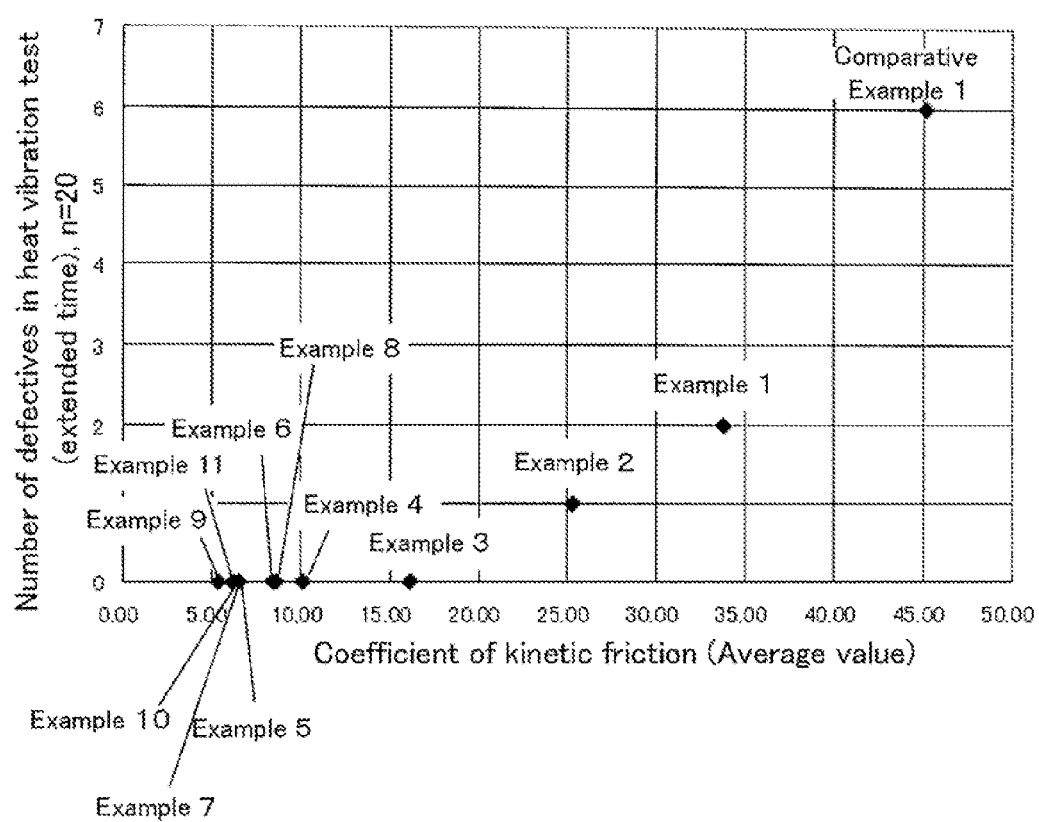
FIG. 26 also illustrates the result of the heat vibration test.
Figure 27:
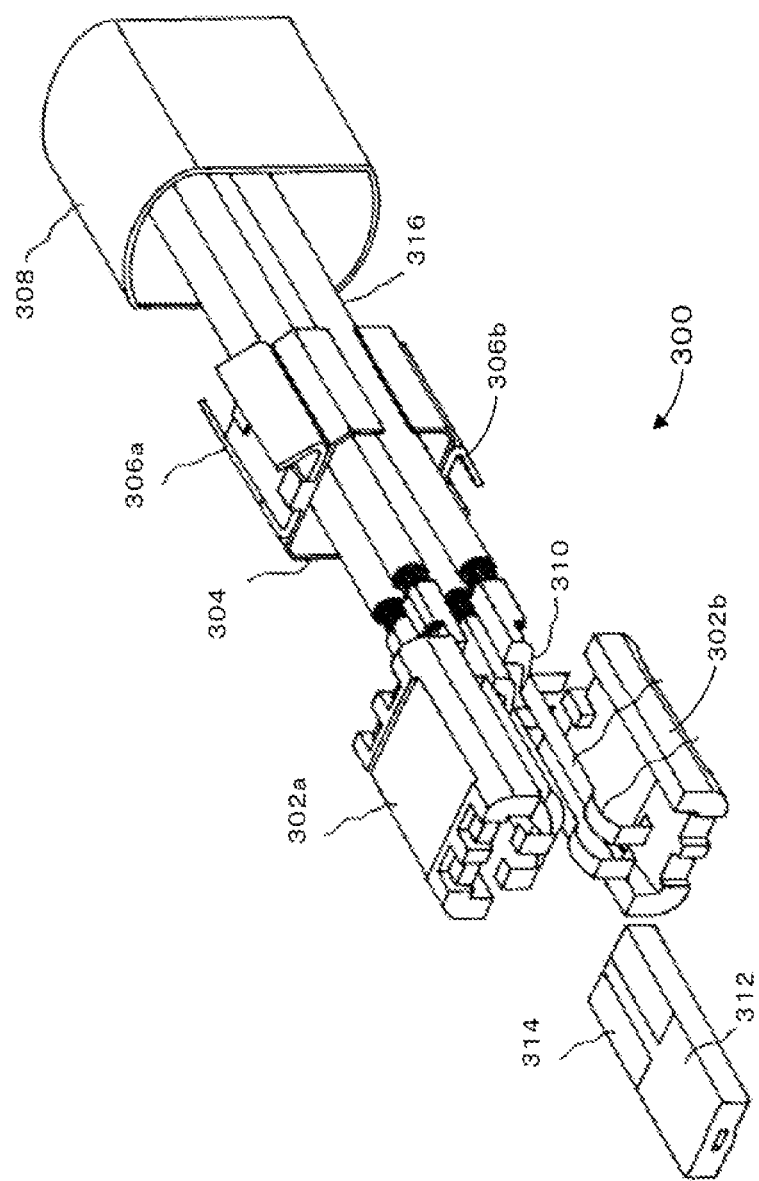
FIG. 27 is an exploded perspective view illustrating a connector 300 of related art.
Figure 28:
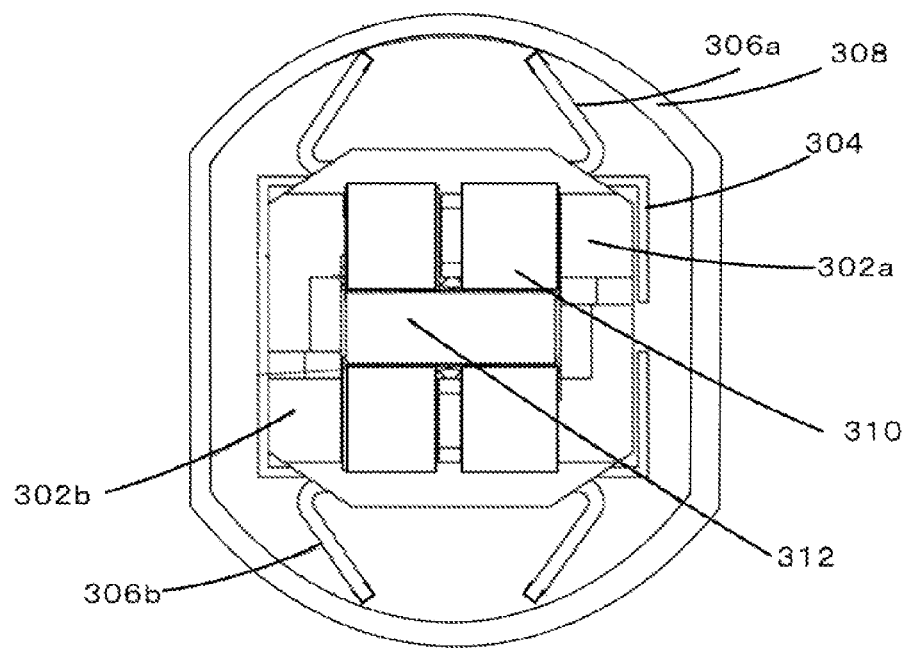
FIG. 28 is a front view of the connector 300 of related art.

A heat vibration test was performed on the gas sensors 10 prepared for Examples 1 to 11 and Comparative Example 1. FIG. 23(a) to FIG. 23(c) illustrate how the heat vibration test was performed. FIG. 23(b) is a diagram as viewed in the direction of D in FIG. 23(a). FIG. 23(c) is a diagram as viewed in the direction of E in FIG. 23(b). As illustrated in FIG. 23, for the heat vibration test, the external thread 41a of the main fitting 41 of the gas sensor 10 was screwed into an internal thread of a stainless pipe 200 to insert the protective cover 30 into the pipe 200, which was then heated by a gas burner 202 and subjected to vibration. The heating conditions were an air-fuel ratio of gas (propane) λ=1.05±0.05, and a heating temperature of 850° C. The vibration conditions were that a 30-minute cycle of vibration (sine wave) with frequency and acceleration of predetermined patterns illustrated in FIG. 24 was repeatedly applied to the pipe 200 for 150 hours. As illustrated, the frequency of the vibration was changed in the range of 50 Hz to 250 Hz, while the acceleration of the vibration was changed in the range of 30 G to 50 G. For each of Examples 1 to 11 and Comparative Example 1, 20 gas sensors 10 were prepared and subjected to the heat vibration test. The result of the heat vibration test is shown in FIG. 25 and FIG. 26. The number of defectives shown in FIG. 25 and FIG. 26 represents the number of gas sensors 10 in which defective contact occurred between the electrodes 21 of the sensor element 20 and the contact fittings 71 during the heat vibration test, out of the 20 gas sensors 10 for each of Examples 1 to 11 and Comparative Example 1. The rotation torque (average value) shown in FIG. 25 represents the average value of torque shown in FIG. 20. The coefficient of kinetic friction (average value) shown in FIG. 26 represents the average value of coefficient of kinetic friction shown in FIG. 22. The occurrence of defective contact was determined by measuring a voltage or a current of the contact fittings 71 to detect the output from the electrodes 21 in the sensor element 20. When the output was interrupted, it was determined that defective contact occurred. In the heat vibration test performed on 12 gas sensors 10 initially prepared in accordance with Comparative Example 1, the number of defectives was 2. Then, the heat vibration test was performed on additional 8 gas sensors 10 prepared in accordance with Comparative Example 1. As shown in FIG. 25 and FIG. 26, the number of defectives was 6 out of the total of 20 gas sensors 10 prepared for Comparative Example 1.

As can be seen from FIG. 25 and FIG. 26, the smaller the rotation torque (coefficient of kinetic friction) or the better the sliding between the inner periphery of the metal tube 95 and the U-springs 92, the smaller the number of defectives in the heat vibration test. In particular, the number of defectives was 0 in Examples 3 to 11. This result shows that the better the sliding between the inner periphery of the metal tube 95 and the U-springs 92, the more it is possible to absorb vibration and the less likely the defective contact will occur between the contact fittings 71 and the sensor element 20.

The present application claims priority from U.S. provisional application No. 61/296,079 filed on Jan. 19, 2010, the entire contents of which are incorporated in the present specification by reference.

INDUSTRIAL APPLICABILITY

A gas sensor according to the present invention can be used in the technical field of sensors for gas detection, such as an $O_2$ sensor, a NOx sensor, and an ammonia gas sensor.

The invention claimed is:

1. A gas sensor comprising:
   a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;
   a plurality of long narrow first contact fittings having conducting portions in contact with the plurality of front-surface electrodes of the sensor element;
   a plurality of long narrow second contact fittings having conducting portions in contact with the plurality of back-surface electrodes of the sensor element;
   a first housing made of ceramic and configured to hold the plurality of first contact fittings such that the first contact fittings are arranged in a direction substantially orthogonal to the length of the first contact fittings and face the plurality of front-surface electrodes;
   a second housing made of ceramic and configured to hold the plurality of second contact fittings such that the second contact fittings are arranged in a direction substantially orthogonal to the length of the second contact fittings and face the plurality of back-surface electrodes;
   a cylindrical metal tube having a central axis along the length of the sensor element and disposed around the first housing and the second housing;
   a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and
   a second elastic member substantially U-shaped in cross section, in contact with the inner periphery of the metal tube at both ends of the U-shape, and configured to press the second housing with an elastic force generated by pressure from the metal tube to bring the second housing closer to the first housing, with the sensor element interposed between the first housing and the second housing,
   wherein an arithmetical mean roughness Ra of the inner periphery of the metal tube is 1 μm or less;
   at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube; and
   at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube.

2. The gas sensor according to claim 1, wherein the sensor element is a planar element.

3. The gas sensor according to claim 1, wherein the arithmetical mean roughness Ra of the inner periphery of the metal tube is 0.8 μm or less.

4. The gas sensor according to claim 1, wherein the inner periphery of the metal tube is plated.

5. The gas sensor according to claim 1, wherein the inner periphery of the metal tube is coated with fluororesin.

6. The gas sensor according to claim 1, wherein the inner periphery of the metal tube is coated with liquid lubricant or solid lubricant.

7. The gas sensor according to claim 1, wherein, in the first elastic member and the second elastic member, the curved surface of the curved contact portion in contact with the inner periphery of the metal tube is plated.

8. The gas sensor according to claim 1, wherein, in the first elastic member and the second elastic member, the curved surface of the curved contact portion in contact with the inner periphery of the metal tube is coated with fluororesin.

9. The gas sensor according to claim 1, wherein, in the first elastic member and the second elastic member, the curved surface of the curved contact portion in contact with the inner periphery of the metal tube is coated with liquid lubricant or solid lubricant.

10. The gas sensor according to claim 1, wherein the metal tube is a member formed by crimping an outer periphery thereof to reduce an inside diameter thereof; and in the first elastic member and the second elastic member, both the ends of the U-shape are positioned off grooves formed in the inner periphery of the metal tube by the crimping.

11. The gas sensor according to claim 1, wherein both the ends of the first elastic member are formed as curved contact portions; and both the ends of the second elastic member are formed as curved contact portions.

12. The gas sensor according to claim 1, wherein the conducting portions of the first contact fittings and the second contact fittings are elastic bodies; and the sensor element is clamped with a pressing force generated by elastic deformation of the conducting portions of the first contact fittings caused by a pressing force applied from the first elastic member through the first housing, and with a pressing force generated by elastic deformation of the conducting portions of the second contact fittings caused by a pressing force applied from the second elastic member through the second housing.

13. The gas sensor according to claim 1, further comprising a third elastic member configured to clamp and press the first housing and the second housing closer to each other.

14. A gas sensor comprising:

a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;

a plurality of long narrow first contact fittings having conducting portions in contact with the plurality of front-surface electrodes of the sensor element;

a plurality of long narrow second contact fittings having conducting portions in contact with the plurality of back-surface electrodes of the sensor element;

a first housing made of ceramic and configured to hold the plurality of first contact fittings such that the first contact fittings are arranged in a direction substantially orthogonal to the length of the first contact fittings and face the plurality of front-surface electrodes;

a second housing made of ceramic and configured to hold the plurality of second contact fittings such that the second contact fittings are arranged in a direction substantially orthogonal to the length of the second contact fittings and face the plurality of back-surface electrodes;

a cylindrical metal tube having a central axis along the length of the sensor element and disposed around the first housing and the second housing;

a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and a second elastic member substantially U-shaped in cross section, in contact with the inner periphery of the metal tube at both, ends of the U-shape, and configured to press the second housing with an elastic force generated by pressure from the metal tube to bring the second housing closer to the first housing, with the sensor element interposed between the first housing and the second housing, wherein the inner periphery of the metal tube is plated, coated with fluororesin, coated with liquid lubricant, or coated with solid lubricant;

at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube; and at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube.

15. A gas sensor comprising:

a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof;

a plurality of long narrow first contact fittings having conducting portions in contact with the plurality of front-surface electrodes of the sensor element;

a plurality of long narrow second contact fittings having conducting portions in contact with the plurality of back-surface electrodes of the sensor element;

a first housing made of ceramic and configured to hold the plurality of first contact fittings such that the first contact fittings are arranged in a direction substantially orthogonal to the length of the first contact fittings and face the plurality of front-surface electrodes;

a second housing made of ceramic and configured to hold the plurality of second contact fittings such that the second contact fittings are arranged in a direction substantially orthogonal to the length of the second contact fittings and face the plurality of back-surface electrodes;

a cylindrical metal tube having a central axis along the length of the sensor element and disposed around the first housing and the second housing;

a first elastic member substantially U-shaped in cross section, in contact with an inner periphery of the metal tube at both ends of the U-shape, and configured to press the first housing with an elastic force generated by pressure from the metal tube to bring the first housing closer to the second housing, with the sensor element interposed between the first housing and the second housing; and a second elastic member substantially U-shaped in cross section, in contact with the inner periphery of the metal tube at both ends of the U-shape, and configured to press the second housing with an elastic force generated by pressure from the metal tube to bring the second housing closer to the first housing, with the sensor element interposed between the first housing and the second housing, wherein at least one of both the ends of the first elastic member is formed as a curved contact portion having a curved surface that is in contact with the inner periphery of the metal tube and has a curvature radius smaller than or equal to a curvature radius of the contact portion of the inner periphery of the metal tube;

at least one of both the ends of the second elastic member is formed as a curved contact portion having a curved surface that is in contact with the inner periphery of the metal tube and has a curvature radius smaller than or equal to a curvature radius of the contact portion of the inner periphery of the metal tube; and in the first elastic member and the second elastic member, the curved surface of the curved contact portion in contact with the inner periphery of the metal tube is plated, coated with fluororesin, coated with liquid lubricant, or coated with solid lubricant.

16. A method for making a gas sensor, comprising the steps of:
   (a) preparing a sensor element capable of detecting a concentration of a predetermined gas component in a gas under measurement, and having a plurality of front-surface electrodes arranged side by side on a front surface thereof and a plurality of back-surface electrodes arranged side by side on a back surface thereof; a plurality of long narrow first contact fittings having conducting portions in contact with the plurality of front-surface electrodes of the sensor element; a plurality of long narrow second contact fittings having conducting portions in contact with the plurality of back-surface electrodes of the sensor element; a first housing made of ceramic and configured to hold the plurality of first contact fittings such that the first contact fittings are arranged in a direction substantially orthogonal to the length of the first contact fittings and face the plurality of front-surface electrodes; and a second housing made of ceramic and configured to hold the plurality of second contact fittings such that the second contact fittings are arranged in a direction substantially orthogonal to the length of the second contact fittings and face the plurality of back-surface electrodes;
   (b) positioning a cylindrical metal tube having an inner periphery with an arithmetical mean roughness Ra of 1 µm or less, a first elastic member substantially U-shaped in cross section and formed such that at least one of both ends of the U-shape is a curved contact portion having a curved surface, and a second elastic member substantially U-shaped in cross section and formed such that at least one of both ends of the U-shape is a curved contact portion having a curved surface, such that the metal tube is disposed around the first housing and the second housing and a central axis of the metal tube is along the length of the sensor element, the first elastic member is disposed between the metal tube and the first housing, and the second elastic member is disposed between the metal tube and the second housing; and
   (c) plastically deforming the metal tube by inwardly pressing the metal tube such that the first elastic member presses the first housing with an elastic force generated when both the ends of the first elastic member are pressed by the metal tube, and brings the first housing closer to the second housing, with the sensor element interposed between the first housing and the second housing; and that the second elastic member presses the second housing with an elastic force generated when both the ends of the second elastic member are pressed by the metal tube, and brings the second housing closer to the first housing, with the sensor element interposed between the first housing and the second housing,
   wherein the curved surface of each of the curved contact portion of the first elastic member and the curved contact portion of the second elastic member is in contact with the inner periphery of the metal tube plastically deformed in the step (c), and a curvature radius of the curved surface is smaller than or equal to a curvature radius of the contact portion of the inner periphery of the metal tube.

* * * * *